(12) United States Patent
Tang et al.

(10) Patent No.: US 7,250,406 B2
(45) Date of Patent: Jul. 31, 2007

(54) COMPOSITIONS AND METHODS FOR THE ACCELERATION OF PROTEIN SECRETION DYNAMICS

(75) Inventors: Shiu-Cheng Tang, Atlanta, GA (US); Athanassios Sambanis, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 571 days.

(21) Appl. No.: 10/419,539

(22) Filed: Apr. 21, 2003

(65) Prior Publication Data

US 2004/0142884 A1 Jul. 22, 2004

Related U.S. Application Data

(60) Provisional application No. 60/374,072, filed on Apr. 19, 2002.

(51) Int. Cl.
- *A01N 43/04* (2006.01)
- *C12Q 1/68* (2006.01)
- *C12N 15/63* (2006.01)
- *C07H 21/02* (2006.01)
- *C07H 21/04* (2006.01)

(52) U.S. Cl. .......................... 514/44; 435/6; 435/91.1; 435/455; 536/23.1; 536/23.5; 536/23.51; 536/24.1; 536/24.5

(58) Field of Classification Search .................... 435/6, 435/91.1, 455, 458, 69.1, 70.1, 375; 536/23.1, 536/23.5, 24.5, 23.51, 24.1; 514/3, 44
See application file for complete search history.

(56) References Cited

U.S. PATENT DOCUMENTS 6,194,176 B1 * 2/2001 Newgard et al. .......... 435/69.4

OTHER PUBLICATIONS

Li, S. et al., Immunity, vol. 8, pp. 135-141 (1998).*
Peracchi, A., Rev. Med. Virol., vol. 14, pp. 47-64 (2004).*
Chirila, T.V., et al., Biomaterials, vol. 23, pp. 321-342 (2002).*
Agrawal, S. et al., Molecualr Med. Today, vol. 6, pp. 72-81 (2000).*
Branch, A.D., Trends in Biochem. Sci., vol. 23, pp. 45-50 (1998).*
Crooke, S.T., Antisense Res. & Appli., Chapter 1, pp. 45-50 (Ed. by S.Crooke, Publ. by Springer-Verlag) (1998).*
Barry, et al., (2001), "Glucose-Regulated Insulin Expression in Diabetic Rats" *Hum Gene Ther.* vol. 12, pp. 131-139.
Byers, P.H., (2002), "Killing the Messenger: New Insights into Nonsense-Mediated mRNA decay" *J. Clin. Invest.* vol. 109, pp. 3-6.
Chen, et al., (2001), "Auto-Regulated Hepatic Insulin Gene Expression in Type 1 Diabetic Rats" *Mol. Ther.* vol. 3, No. 4, pp. 584-590.
Clayton, C.E., (2002), "Life without Transcriptional Control? From Fly to Man and Back Again" *The EMBO Journal* vol. 21, No. 8, pp. 1881-1888.

Dong, H. & S.L. Woo, (2001), "Hepatic Insulin Production for Type 1 Diabetes" *Trends Endocrinol. Metab.* vol. 12, No. 10, pp. 441-446.
Efrat, S., (1998), "Prospects for Gene Therapy of Insulin-Dependent Diabetes Mellitus" *Diabetologia* vol. 41, No. 12, pp. 1401-1409.
Groskreutz, et al., C.M., (1994), "Genetically Engineered Proinsulin Constitutively Processed and Secreted as Mature, Active Insulin" *J. Biol. Chem.* vol. 269, No. 8, pp. 6241-6245.
Guhaniyogi, J. & G. Brewer, (2001), "Regulation of mRNA Stability in Mammalian Cells" *Gene* 265, pp. 11-23.
Hentze, M.W. & A.E. Kulozik, (1996), "A Perfect Message: RNA Surveillance and Nonsense-Mediated Decay" *Cell.* vol. 96, pp. 307-310.
Lee, et al., (2002), "Remission in Models of Type 1 Diabetes by Gene Therapy Using a Single-Chain Insulin Analogue" *Nature* vol. 408, pp. 483-488.
Li, S. & M.F. Wilkinson, (1998), "Nonsense Surveillance in Lymphocytes?" *Immunity* vol. 8, pp. 135-141.
Maquat, L.E., (2002), "Nonsense-Mediated mRNA Decay" *Curr. Biol.* vol. 12, No. 6, pp. R196-R197.
Pulak, R. & P. Anderson, (1993), "mRNA Surveillance by the *Caenorhabditis elegans smg* genes" *Genes Dev.* vol. 7, Nos. 9-12, pp. 1885-1897.
Tang, S. C. & A. Sambanis, (2003), "Preproinsulin mRNA Engineering and its Application to the Regulation of Insulin Secretion from Human Hepatomas" *FEBS Letters* 537, pp. 193-197.
Taniguchi, H., et al., (1996), "Control of Proinsulin Production By Sense-Anti-Sense Regulation In Response to Glucocorticoids" *Cell Transplantation* vol. 5, pp. S55-S57.
Thulè, et al., (2000), "Glucose Regulated Production of Human Insulin in Rat Hepatocytes" *Gene Ther.* vol. 7, pp. 205-214.
Thulè, P.M. & J-M, Liu, (2000), "Regulated Hepatic Insulin Gene Therapy of STZ-Diabetic Rats" *Gene Ther.* vol. 7, pp. 1744-1752.
van Hoof, A. & R. Parker. (2002), "Messenger RNA Degradation: Beginning at the End." *Curr. Biol.* vol. 12, pp. R285-R287.
Wilusz, C.J., et al. (2001), "Curbing the Nonsense: the Activation and Regulation of mRNA Surveillance" *Genes Dev.* vol. 15, No. 21, pp. 2781-2916.
Hillman, et al., 2004, "An Unappreciated Role for RNA Surveillance", *Genome Biology*, 5(2):1-16.
Wicksteed, et al., 2001, "Cooperativity between the Preproinsulin mRNA Untranslated Regions is Necessary for Glucose-Stimulated Translation", *The Journal of Biological Chemistry*, 276(25): 22553-22558.

* cited by examiner

*Primary Examiner*—Jane Zara
(74) *Attorney, Agent, or Firm*—Sutherland Asbill & Brennan LLP

(57) ABSTRACT

The present invention provides compositions and methods for modulating the secretion of transcriptionally regulated proteins from recombinant cells. More particularly, the present invention provides compositions and methods for accelerating the secretion dynamics of human insulin from recombinant cells using nonsense mediated mRNA decay of the preproinsulin mRNA transcript.

55 Claims, 9 Drawing Sheets

SEQUENCE LISTING

```
<160> NUMBER OF SEQ ID NOS: 11

<210> SEQ ID NO 1
<211> LENGTH: 137
<212> TYPE: DNA
<213> ORGANISM: Artificial Sequence
<220> FEATURE:
<223> OTHER INFORMATION: Description of Artificial Sequence: Synthetic
                        chimeric intron sequence

<400> SEQUENCE: 1
caggtaagta tcaaggttac aagacaggtt taaggagacc aatagaaact gggcttgtcg      60
agacagagaa gactcttgcg tttctgatag gcacctattg gtcttactga catccacttt     120
gcctttctct ccacagg                                                    137

<210> SEQ ID NO 2
<211> LENGTH: 333
<212> TYPE: DNA
```

<213> ORGANISM: Homo sapiens

<400> SEQUENCE: 2

```
atggccctgt ggatgcgcct cctgcccctg ctggcgctgc tggccctctg gggacctgac      60
ccagccgcag cctttgtgaa ccaacacctg tgcggatccg acctggtgga agctctctac    120
ctagtgtgcg gggaacgagg cttcttctac acacccagga ccaagcggga ggcagaggac    180
ctgcaggtgg ggcaggtgga gctgggcggg ggccctggtg caggcagcct gcagcccttg    240
gccctggagg gatcccggca agcgtggc attgtggaac aatgctgtac cagcatctgc      300
tccctctacc agctggagaa ctactgcaac tag                                  333
```

<210> SEQ ID NO 3
<211> LENGTH: 1080
<212> TYPE: DNA
<213> ORGANISM: Homo sapiens

<400> SEQUENCE: 3

```
ctagagtcga cctgcagaag cttaccatgg ccctgtggat gcgcctcctg cccctgctgg      60
cgctgctggc cctctgggga cctgaccag ccgcagcctt tgtgaaccaa cacctgtgcg     120
gatccgacct ggtggaagct ctctacctag tgtgcgggga acgaggcttc ttctacacac    180
ccaggaccaa gcgggaggca gaggacctgc aggtggggca ggtggagctg gcgggggcc    240
ctggtgcagg cagcctgcag cccttggccc tggagggatc ccggcagaag cgtggcattg    300
tggaacaatg ctgtaccagc atctgctccc tctaccagct ggagaactac tgcaactagt    360
ctagagtcga cctgcagaag cttaccatgg ccctgtggat gcgcctcctg cccctgctgg    420
cgctgctggc cctctgggga cctgaccag ccgcagcctt tgtgaaccaa cacctgtgcg    480
gatccgacct ggtggaagct ctctacctag tgtgcgggga acgaggcttc ttctacacac    540
ccaggaccaa gcgggaggca gaggacctgc aggtggggca ggtggagctg gcgggggcc    600
ctggtgcagg cagcctgcag cccttggccc tggagggatc ccggcagaag cgtggcattg    660
tggaacaatg ctgtaccagc atctgctccc tctaccagct ggagaactac tgcaactaga    720
gtcgacctgc agaagcttac catggccctg tggatgcgcc tcctgcccct gctggcgctg    780
ctggccctct ggggacctga cccagccgca gcctttgtga accaacacct gtgcggatcc    840
gacctggtgg aagctctcta cctagtgtgc ggggaacgag gcttcttcta cacacccagg    900
accaagcggg aggcagagga cctgcaggtg gggcaggtgg agctggcgg gggcctggt    960
gcaggcagcc tgcagccctt ggccctggag ggatcccggc agaagcgtgg cattgtggaa   1020
caatgctgta ccagcatctg ctccctctac cagctggaga actactgcaa ctagtctaga   1080
```

<210> SEQ ID NO 4
<211> LENGTH: 1217
<212> TYPE: DNA
<213> ORGANISM: Homo sapiens

<400> SEQUENCE: 4

```
caggtaagta tcaaggttac aagacaggtt taaggagacc aatagaaact gggcttgtcg      60
agacagagaa gactcttgcg tttctgatag gcacctattg gtcttactga catccacttt    120
gcctttctct ccacaggcta gagtcgacct gcagaagctt accatggccc tgtggatgcg    180
cctcctgccc ctgctggcgc tgctggccct ctggggacct gacccagccg cagcctttgt    240
gaaccaacac ctgtgcggat ccgacctggt ggaagctctc tacctagtgt gcggggaacg    300
aggcttcttc tacacaccca ggaccaagcg ggaggcagag gacctgcagg tggggcaggt    360
```

```
ggagctgggc gggggccctg gtgcaggcag cctgcagccc ttggccctgg agggatcccg    420
gcagaagcgt ggcattgtgg aacaatgctg taccagcatc tgctccctct accagctgga    480
gaactactgc aactagtcta gagtcgacct gcagaagctt accatggccc tgtggatgcg    540
cctcctgccc ctgctggcgc tgctggccct ctggggacct gacccagccg cagcctttgt    600
gaaccaacac ctgtgcggat ccgacctggt ggaagctctc tacctagtgt gcggggaacg    660
aggcttcttc tacacaccca ggaccaagcg ggaggcagag gacctgcagg tggggcaggt    720
ggagctgggc gggggccctg gtgcaggcag cctgcagccc ttggccctgg agggatcccg    780
gcagaagcgt ggcattgtgg aacaatgctg taccagcatc tgctccctct accagctgga    840
gaactactgc aactagagtc gacctgcaga agcttaccat ggccctgtgg atgcgcctcc    900
tgcccctgct ggcgctgctg gccctctggg gacctgaccc agccgcagcc tttgtgaacc    960
aacacctgtg cggatccgac ctggtggaag ctctctacct agtgtgcggg gaacgaggct   1020
tcttctacac acccaggacc aagcgggagg cagaggacct gcaggtgggg caggtggagc   1080
tgggcggggg ccctggtgca ggcagcctgc agcccttggc cctggaggga tcccggcaga   1140
agcgtggcat tgtggaacaa tgctgtacca gcatctgctc cctctaccag ctggagaact   1200
actgcaacta gtctaga                                                   1217
```

<210> SEQ ID NO 5
<211> LENGTH: 110
<212> TYPE: PRT
<213> ORGANISM: Homo sapiens

<400> SEQUENCE: 5

```
Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
                20                  25                  30

Ser Asp Leu Val Glu Ala Leu Tyr Leu Val Cys Gly Glu Arg Gly Phe
            35                  40                  45

Phe Tyr Thr Pro Arg Thr Lys Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Arg Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 6

```
tccgacctgg tggaagctct ctacctagtg                                       30
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

```
<400> SEQUENCE: 7
tttgtgaacc aacacctgtg c                                              21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
gggtgtgtag aagaagcctc gtt                                            23

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Probe

<400> SEQUENCE: 9
cccgtaaact cgcccagaag ctaggtgt                                       28

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
ggtcggaatc gaaggtttaa ca                                             22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
tgccaataca atgtaggctg ct                                             22
```

COMPOSITIONS AND METHODS FOR THE ACCELERATION OF PROTEIN SECRETION DYNAMICS

CROSS REFERENCE TO RELATED APPLICATIONS

The present invention claims the priority benefit of U.S. Provisional Patent Application Ser. No. 60/374,072, filed on Apr. 19, 2002, the entire contents of which are hereby incorporated by reference.

ACKNOWLEDGMENT OF FEDERAL RESEARCH SUPPORT

This invention was made, at least in part, with funding from the National Science foundation (Award Number EEC-9731643). Accordingly, the United States Government has certain rights in this invention.

BACKGROUND OF THE INVENTION

1. Field of the Invention

The field of this invention is techniques to modulate the dynamics of transcriptionally regulated protein secretion and mRNA stability. These techniques are of particular use for improving the dynamics of insulin secretion, which is a useful tool in cell-based therapies for insulin-dependent diabetes.

2. Background Art

Cell-based therapies for treating insulin-dependent diabetes (IDD) can provide a more physiologic regulation of blood glucose levels in a less invasive fashion than daily insulin injections. Cell sourcing constitutes a critical issue in developing a cell-based therapy for treatment of IDD. Genetic engineering of non-$\beta$ cells, particularly those of hepatic origin, for glucose-responsive insulin secretion offers significant promise in developing a cell-based therapy for insulin-dependent diabetes. Responsiveness to physiologic stimuli is introduced at the gene transcription level by using promoters up-regulated by glucose and possibly down-regulated by insulin (Thulé, et al., 2000 Gene Ther. 7:205-14; Thulé, P. M. & Liu, J. M., 2000 Gene Ther. 7:1744-52; Lee, et al., 2000 Nature 408:483-8; Barry, et al., 2001 Hum. Gene Ther. 12:131-9; Chen, et al., 2001 Mol. Ther. 3:584-90).

Based on this concept, glucose-regulated insulin expression has been achieved in streptozotocin (STZ)-induced diabetic rodents (Thulé, P. M. & Liu, J. M., 2000 Gene Ther. 7:1744-52; Lee, et al., 2000 Nature 408:483-8; Barry, et al., 2001 Hum. Gene Ther. 12:131-9; Chen, et al., 2001 Mol. Ther. 3:584-90). A major advantage of these cells is that they are potentially autologous, retrieved as a biopsy from the patient. A disadvantage of these cells is that transcriptionally controlled cells exhibit sluggish secretion dynamics and thus may not be suitable, as such, for achieving normoglycemia in higher diabetic animals and humans. To expedite the dynamics of secretion down-regulation, translation needs to stop soon after transcription has been turned off. Of particular significance is the slow dynamics of secretion down-regulation, which result in the cells secreting insulin long after the stimulus has been removed and treatment with these cells may thus revert diabetes to hyperinsulinemia and hypoglycemia, a serious pathological condition.

It has been suggested that the prolonged stability of preproinsulin (PPI) mRNA causes the sluggishness of secretion down-regulation (Efrat, S., 1998, Diabetologia 41:1401-9; Dong, H. & Woo, S. L., 2001 Trends Endocrinol. Metab. 12:441-6). Although prior reports on the PPI MRNA half-life in non-$\beta$ cells are limited, data from normal and transformed $\beta$ cells strongly indicate that the stability of PPI mRNA is a limiting factor in expediting secretion down-regulation. In isolated primary rat islets, the half-life of PPI mRNA was estimated to be 77 hours under high glucose (17 mM) and 29 hours under low glucose concentration (3.3 mM) (Nielsen, et al., 1985, J. Biol. Chem. 260:13585-9). In $\beta$TC-3 insulinomas, there was only marginal PPI mRNA degradation over 24 hours after transcription was stopped (Schuppin, G. T. & Rhodes, C. J., 1996, Biochem. J. 313:259-68), while the half-life of PPI mRNA in RIN-5F insulinomas was found to be 58 hours and 26 hours under high (20 mM) and low (3 mM) glucose concentration, respectively (Nielsen, et al., 1985, J. Biol. Chem. 260: 13585-9).

The topic of modulation of mRNA stability is currently under intense investigation (Guhaniyogi, J. & Brewer, G., 2001, Gene 265:11-23; Clayton, C.E., 2002, Embo. J. 21:1881-8; van Hoof, A. & Parker, R., 2002, Curr. Biol. 12:R285-7). Specifically with PPI mRNA, to accelerate the rate of mRNA turnover, the use of anti-sense RNA (Taniguchi, K., et al., 1996, Cell Transplant 5:S55-7) or connecting the insulin gene with the 3'-untranslated region (3'-UTR) of some labile mRNAs, such as those encoding cytokines, have been considered (Dong, H. & Woo, S. L., 2001, Trends Endocrinol. Metab. 12:441-6). However, these systems require the use of more than one construct, or have not shown to be entirely successful.

Recently, nonsense-mediated mRNA decay (NMD) has received significant attention because of its biological and medical importance (Hentze, M. W. & Kulozik, A. E., 1999, Cell 96:307-10; Wilusz, C. J., Wang, W. and Peltz, S. W., 2001, Genes Dev. 15:2781-5; Byers, P. H., 2002, J. Clin. Invest. 109; 3-6; Maquat, L. E., 2002, Curr. Biol. 12, R196-7). Mutant mRNAs with premature stop codons can be detected by cells via a surveillance mechanism, and are subjected to NMD (Li, S. & Wilkinson, M. F., 1998, Immunity 8,135-41; Pulak, R. & Anderson, P., 1993, Genes Dev. 7, 1885-97). NMD likely evolved in vivo to eliminate erratic mRNAs.

Because of the difficulty in modulating the dynamics of protein secretion in general, and insulin secretion specifically, there is a need in the art for techniques to improve the efficiency and dynamics of protein secretion from a recombinant cell.

SUMMARY OF THE INVENTION

It is an object of the present invention to overcome, or at least alleviate, one or more of the difficulties or deficiencies associated with the prior art. In that regard, the present invention provides compositions and methods to improve and modulate the dynamics of protein secretion from a recombinant cell, generally, and preferably, to modulate the dynamics of insulin secretion from a recombinant cell. The methods and compositions provided herein allow for the modulation of the dynamics of protein secretion using one construct, which greatly simplifies the process of modulating protein secretion.

The invention provided herein encompasses a nucleic acid producing a nonsense mediated mRNA transcript encoding a transcriptionally regulated protein, such as insulin, wherein the nonsense mediated mRNA transcript has a shorter half-life than an mRNA encoding the transcriptionally regulated protein that is not nonsense mediated. In a preferred embodiment, the nonsense mediated mRNA transcript comprises a premature termination signal. Preferably, the premature termination signal comprises a stop codon of the portion of the mRNA transcript encoding the transcriptionally regulated protein, a polyadenylation sequence and a supplementary nucleic acid sequence inserted between the stop codon and the polyadenylation sequence.

The invention provided herein further encompasses a mammalian non-β cell comprising a heterologous nucleic acid which produces a nonsense mediated mRNA transcript encoding a transcriptionally regulated insulin protein, wherein the insulin protein is secreted by the cell and the nonsense mediated mRNA transcript has a shorter half-life than an mRNA encoding the transcriptionally regulated insulin protein that is not nonsense mediated. In a preferred embodiment, the non-β cell is a human hepatic cell.

The invention further provides a method for down-regulating secretion of a transcriptionally regulated protein. In one embodiment, the method comprises a) introducing a heterologous nucleic acid into a cell, wherein the nucleic acid transcribes a nonsense mediated mRNA transcript which encodes the transcriptionally regulated protein; and b) expressing the heterologous nucleic acid to produce the nonsense mediated mRNA transcript encoding the transcriptionally regulated protein, such that the protein is secreted by the cell and the nonsense mediated mRNA transcript has a shorter half-life than an mRNA encoding the transcriptionally regulated protein that is not nonsense mediated; to thereby down-regulate secretion of the protein. The invention further provides a method of modulating the secretion dynamics of insulin by promoting degradation of preproinsulin MRNA, comprising introducing a heterologous nucleic acid into a non-β cell, wherein the heterologous nucleic acid comprises a preproinsulin-encoding polynucleotide operatively linked to a promoter, and an mRNA transcript transcribed from the heterologous nucleic acid comprises a premature termination signal, thereby modulating the secretion dynamics of insulin by promoting degradation of preproinsulin mRNA transcripts. In a preferred embodiment, the transciptionally regulated protein is human insulin. In one embodiment, the nonsense mediated mRNA transcript comprises a premature termination signal, comprising a stop codon of the mRNA transcript encoding the transcriptionally regulated polypeptide, a polyadenylation sequence and a supplementary nucleic acid sequence inserted between the stop codon and the polyadenylation sequence.

BRIEF DESCRIPTION OF THE DRAWINGS

FIG. 3A shows the down-regulation of PPI mRNA, while

FIG. 7A shows the result of using the Tet-Off system to evaluate the down-regulation of insulin secretion with different copies (1 to 4) of the preproinsulin gene. Transcription was down-regulated by adding DOX at time 0. FIG. 7B demonstrates the dynamics of insulin secretion in an impulse test when cells transfected with Tet-On system containing 1-4 copies of the preproinsulin gene were exposed to a square wave of DOX induction for 1 hour, followed by basal conditions for 7 hours.

DETAILED DESCRIPTION OF THE INVENTION

Figure 1:
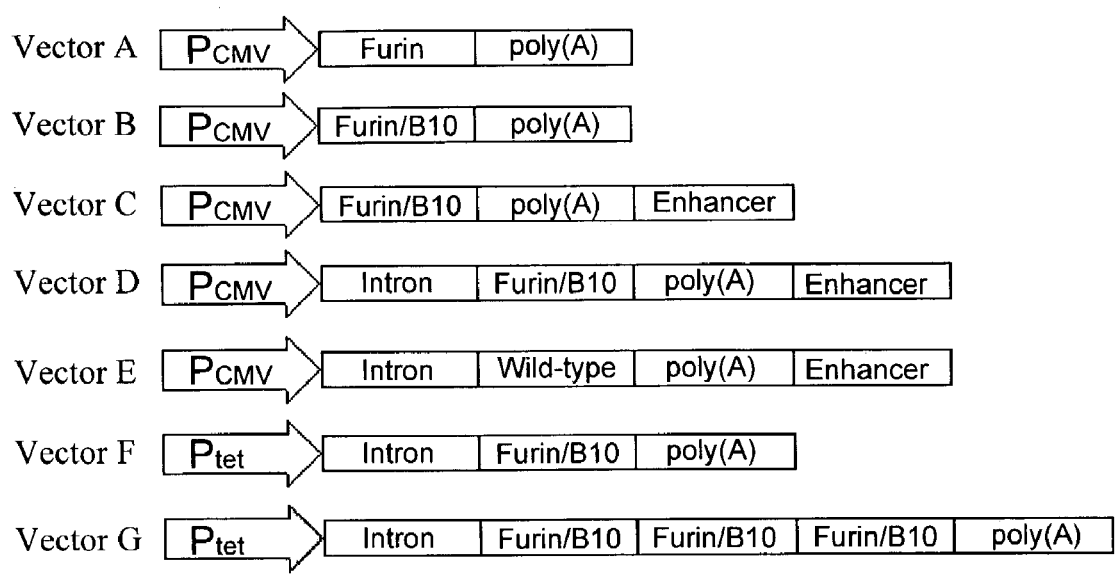
FIG. 1 provides schematics of the structures of the plasmids used for insulin expression. Vectors A, B, C, D and E were constructed for evaluating elements that increase insulin expression. Vectors F and G are the Tet-responsive plasmids with one and three copies, respectively, of PPI cDNA.

Applicant has demonstrated that nucleic acids producing a nonsense mediated mRNA transcript encoding a transcriptionally regulated insulin protein and cells containing these nucleic acids result in the improved modulation of protein secretion from a recombinant cell compared to nucleic acids that do not produce a nonsense mediated mRNA transcript. The methods and compositions encompassed by the present invention allow for the modulation of the dynamics of protein secretion using one construct, which greatly simplifies the process of modulating protein secretion compared to other known techniques, such as the use of anti-sense or RNA interference technologies.

The invention provided herein encompasses a nucleic acid producing a nonsense mediated mRNA transcript encoding a transcriptionally regulated protein, such as insulin, wherein the nonsense mediated mRNA transcript has a shorter half-life than an mRNA encoding the transcriptionally regulated protein that is not nonsense mediated.

The invention provided herein further encompasses a mammalian non-β cell comprising a heterologous nucleic acid which produces a nonsense mediated mRNA transcript encoding a transcriptionally regulated insulin protein, wherein the insulin protein is secreted by the cell and the nonsense mediated mRNA transcript has a shorter half-life than an mRNA encoding the transcriptionally regulated insulin protein that is not nonsense mediated. In a preferred embodiment, the non-β cell is a human hepatic cell.

The invention further provides a method for down-regulating secretion of a transcriptionally regulated protein. In one embodiment, the method comprises a) introducing a heterologous nucleic acid into a cell, wherein the nucleic acid transcribes a nonsense mediated mRNA transcript which encodes the transcriptionally regulated protein; and b) expressing the heterologous nucleic acid to produce the nonsense mediated mRNA transcript encoding the transcriptionally regulated protein, such that the protein is secreted by the cell and the nonsense mediated mRNA transcript has a shorter half-life than an mRNA encoding the transcriptionally regulated protein that is not nonsense mediated; to thereby down-regulate secretion of the protein. The invention further provides a method of modulating the secretion dynamics of insulin by promoting degradation of preproinsulin mRNA, comprising introducing a heterologous nucleic acid into a non-β cell, wherein the heterologous nucleic acid comprises a preproinsulin-encoding polynucleotide operatively linked to a promoter, and an mRNA transcript transcribed from the heterologous nucleic acid comprises a premature termination signal, thereby modulating the secretion dynamics of insulin by promoting degradation of preproinsulin mRNA. In a preferred embodiment, the transcriptionally regulated protein is human insulin.

In a preferred embodiment of the above described compositions and methods, the nonsense mediated mRNA transcript comprises a premature termination signal. Preferably, the premature termination signal comprises a stop codon of the portion of the MRNA transcript encoding the transcriptionally regulated protein, a polyadenylation sequence and a supplementary nucleic acid sequence inserted between the stop codon and the polyadenylation sequence.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 *Glossary of genetics: classical and molecular,* 5th Ed., Berlin: Springer-Verlag; and in *Current Protocols in Molecular Biology,* F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

The invention provides nucleic acids expressing a nonsense mediated mRNA transcript encoding a transcriptionally regulated protein, such as insulin. In a preferred embodiment, the nucleic acid sequences of the present invention are produced by recombinant DNA techniques. For example, a nucleic acid molecule encoding the transcriptionally regulated polypeptide is cloned into a vector (as described below), the vector is introduced into a host cell (as described below) and the transcriptionally regulated polypeptide is expressed in the host cell or the nucleic acid may insert into the genome of the host cell. The transcriptionally regulated polypeptide, or the nucleic acid encoding the transcriptionally regulated polypeptide can then be isolated from the cells by an appropriate purification scheme using standard polypeptide purification techniques. Alternately, the expression levels of the heterologous nucleotide can be determined using techniques well known in the art, such as by Northern blot. For the purposes of the invention, the term "recombinant nucleic acid" refers to a polynucleotide that has been altered, rearranged or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations.

As used herein, the term "recombinant nucleic acid molecule" refers to one which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

In a preferred embodiment, the nucleic acid of the present invention is a heterologous nucleic acid encoding a transcriptionally regulated protein. As used herein, the term "heterologous nucleic acid" refers to a nucleic acid that has been isolated and is introduced into a host cell using any known or later developed recombinant DNA technique known to those of ordinary skill in the art. An "isolated" nucleic acid molecule is one that is substantially separated from other nucleic acid molecules that are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated, as is a cDNA molecule. In various embodiments, the isolated transcriptionally regulated polypeptide or nucleotide sequence encoding the transcriptionally regulated polypeptide can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a mammalian, or a human cell). A nucleic acid is also considered isolated if it has been altered by human intervention, or placed in a locus or location that is not its natural site, or if it is introduced into a cell by transfection. Moreover, an "isolated" nucleic acid molecule can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention can be isolated using standard molecular biology techniques and the sequence information provided herein. For example, a nucleic acid molecule encoding a mammalian preproinsulin can be isolated by the polymerase chain reaction using oligonucleotide primers designed based upon a known preproinsulin sequence. For example, MRNA can be isolated from a mammalian cell and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a nucleotide sequence of interest can be prepared by standard synthetic techniques, e.g., using an automated DNA synthesizer. These cDNAs may comprise sequences encoding the nucleic acid of interest, (i.e., the "coding region" of preproinsulin), as well as 5' untranslated sequences and 3' untranslated sequences.

In one embodiment of the present invention, the heterologous nucleic acid comprises a nucleic acid sequence encoding an intron as defined in SEQ ID NO:1, connected to a nucleic acid sequence encoding a mutated preproinsulin as defined in SEQ ID NO:2. In a further preferred embodiment, the heterologous nucleic acid comprises a nucleic acid sequence as defined in SEQ ID NO:1, connected to a nucleic acid sequence encoding three copies of the mutated PPI as defined in SEQ ID NO:3. The nucleic acid sequence as defined in SEQ ID NO:1, connected to a nucleic acid sequence as defined in SEQ ID NO:3, is defined in SEQ ID NO:4. In other embodiments, the heterologous nucleic acid sequence comprises SEQ ID NO:3, optionally linked to an intron. The intron can be located upstream or downstream of the nucleic acid sequence. In other embodiments the heterologous nucleic acid comprises a nucleic acid sequence that encodes a polypeptide as defined in SEQ ID NO:5, or orthologs or homologs thereof. In other embodiments, the heterologous nucleic acid comprises a nucleic acid sequence that encodes wild-type insulin. In another embodiment, the heterologous nucleic acid comprises a plurality of copies of the human preproinsulin gene. In still another embodiment, the heterologous nucleic acid comprises one or more copies of the human preproinsulin gene. Preferably, if the heterologous nucleic acid comprises one copy of the human preproinsulin gene, it additionally comprises a premature termination signal comprising a supplementary nucleic acid sequence inserted after the stop codon of the preproinsulin gene and inserted before the sequence signaling for the addition of the poly-A tail. In another embodiment, the heterologous nucleic acid comprises one copy of the human preproinsulin gene and comprises a plurality of copies of a nucleic acid sequence that has greater than 90% homology to the human preproinsulin gene. It is to be understood that while the furin mutated preproinsulin gene was used in the examples described herein, the use of a wild-type preproinsulin gene and homologs and orthologs thereof is also encompassed by the present invention.

As used herein, a "gene" is the fundamental physical and functional unit of heredity. In biochemical terms, a gene is an ordered sequence of nucleotides located in a particular position on a particular chromosome that encodes a specific functional product (i.e., a protein or RNA molecule). As used herein, a gene is composed not only of coding sequences but can comprise adjacent DNA regions involved in control of the transcription of the coding sequences (e.g., promoters, enhancers) and introns.

The heterologous nucleic acid of the present invention transcribes a nonsense mediated mRNA transcript which encodes a transcriptionally regulated protein. As used herein, a "nonsense mediated mRNA transcript" refers to a mRNA transcript that has a shorter half-life than an mRNA transcript that is not nonsense mediated. Methods to determine the half-life of an mRNA transcript or a population of mRNA transcripts are well known to those of ordinary skill in the art. The half-life of a nonsense mediated mRNA transcript is shorter due to nonsense mediated mRNA decay. As used herein, the term "nonsense mediated mRNA decay" refers to a surveillance mechanism in a cell that serves to eliminate mRNA transcripts that have premature termination codons or otherwise have an abnormal length of nucleotide sequence between the termination codon and the polyadenylation signal (for review, see Hentze & Kulozik, 1999 Cell 96:307-310; Byers, 2002 J. Clin. Invest. 109:3-6; Maquat, 2002 Curr. Biol. 12(6):R196-7). As used herein, the term "abnormal length" refers to a length of nucleotide sequences that is not naturally found interposed between the termination codon and the polyadenylation signal.

In a preferred embodiment of the present invention, nonsense mediated mRNA decay is induced by the presence of a premature termination signal in the mRNA transcript that encodes for a transcriptionally regulated protein. Preferably, the premature termination signal comprises a stop codon of the portion of the mRNA transcript encoding the transcriptionally regulated protein, a polyadenylation sequence and a supplementary nucleic acid sequence inserted between the stop codon and the polyadenylation sequence. As used herein, the term "premature termination signal" refers to a combination of sequences that serves to indicate to the cell that the resultant protein will be truncated, and serves to induce nonsense mediated mRNA decay. The use of the term "premature" in this sense does not necessarily indicate that the stop codon of the portion of the mRNA transcript encoding the transcriptionally regulated protein has been changed or moved upstream; it merely indicates that the surveillance mechanism of a cell perceives that the stop codon is in a premature position.

In a preferred embodiment, the surveillance mechanism of the cell perceives that the stop codon of the portion of the mRNA transcript that encodes for the transcriptionally regulated protein is premature due to the presence of a supplementary nucleic acid that has been inserted between the stop codon and the sequence signaling for cleavage of the mRNA and the addition of a polyA sequence. As used herein, the term "supplementary nucleic acid" refers to the addition of nucleic acid sequences that are not naturally located immediately upstream of the poly-A sequence. In one embodiment, the supplementary nucleic acid sequence is one or more copies of the preproinsulin gene. In another embodiment, the supplementary nucleic acid comprises a gene encoding a transcriptionally regulated protein. In another embodiment, the supplementary nucleic acid is a coding region of a gene. In another embodiment, the supplementary nucleic acid is a cDNA sequence that encodes for a protein. In still other embodiments, the supplementary nucleic acid is non-coding. Specifically excluded from the definition of a "supplementary nucleic acid" are AU-rich elements from the 3' UTR of a highly labile mRNA, such as from a cytokine, IGFBP-1, and proto-oncogenes.

In preferred embodiments of the present invention, the supplementary nucleic acid comprises a nucleic acid sequence of approximately 50-3000 bp, more preferably, of between approximately 200-2500 bp, and still more preferably of between approximately 350-1650 bp. In a preferred embodiment, the supplementary nucleic acid comprises a nucleic acid sequence of approximately 600-1050 bp, more preferably comprises a nucleic acid sequence of approximately 600-800 bp, and more preferably comprises a nucleic acid sequence of approximately 700 bp in length. In other embodiments of the present invention, the stop codon of the portion of the mRNA transcript encoding the transcriptionally regulated protein is located approximately 50-3000 nucleotides upstream of the polyadenylation sequence, more preferably approximately 200-2500 nucleotides upstream of the polyadenylation sequence, more preferably approximately 350-1650 nucleotides upstream of the polyadenylation sequence, more preferably approximately 600-1050 nucleotides upstream of the polyadenylation sequence, more preferably approximately 600-800 nucleotides upstream of the polyadenylation sequence, and still more preferably approximately 700 nucleotides upstream of the polyadenylation sequence.

The nucleic acids of the present invention encode for a transcriptionally regulated protein. As used herein, the term "protein" is synonymous with the term "polypeptide." As used herein, the term "polypeptide" refers to a chain of at least four amino acids joined by peptide bonds. The chain may be linear, branched, circular or combinations thereof. As used herein, a "transcriptionally regulated protein" refers to a protein whose production is regulated at the level of transcription, or the production of mRNA. Transcriptional regulation is controlled by transcriptional response elements such as promoters, enhancers, or other regulatory elements. Any one of many different elements located in a transcriptional response element can independently activate or repress transcription of a gene. For example, the transcription of preproinsulin in β cells is activated by glucose and down-regulated by insulin. While the compositions and methods of the present invention encompass all transcriptionally regulated proteins, in a preferred embodiment of the present invention, the transcriptionally regulated protein is insulin. More preferably, the transcriptionally regulated protein is human insulin.

The invention also provides chimeric or fusion polypeptides. As used herein, a "chimeric polypeptide" or "fusion polypeptide" comprises a nucleotide sequence encoding a transcriptionally regulated protein operatively linked to a nucleotide sequence that does not encode a transcriptionally regulated protein, or that is linked to a nucleic acid sequence that encodes a different transcriptionally regulated protein. As used herein with respect to the fusion polypeptide, the term "operatively linked" is intended to indicate that the nucleotide sequence encoding a transcriptionally regulated protein and the nucleotide sequence it is linked to are fused to each other so that both sequences fulfill the proposed function attributed to the sequence used. The nucleotide sequence not encoding a transcriptionally regulated protein or encoding a different protein can be fused to the N-terminus or C-terminus of the nucleotide sequence encoding a transcriptionally regulated protein. For example, in one embodiment, the fusion polypeptide is a GST-transcriptionally regulated protein fusion polypeptide in which the transcriptionally regulated protein sequences are fused to the C-terminus of the GST sequences. Such fusion polypeptides can facilitate the purification of recombinant transcriptionally regulated proteins. In another embodiment, the fusion polypeptide is a transcriptionally regulated protein containing a heterologous signal sequence at its N-terminus. In certain host cells (e.g., mammalian host cells), expression and/or secretion of a transcriptionally regulated protein can be increased through use of a heterologous signal sequence. In another embodiment, the fusion polypeptide is a transcriptionally regulated protein operatively linked to a nucleic acid encoding a detectable signal peptide, such as, but not limited to, luciferase.

Preferably, a transcriptionally regulated chimeric or fusion polypeptide of the invention is produced by standard recombinant DNA techniques. For example, DNA fragments coding for the different polypeptide sequences are ligated together in-frame in accordance with conventional techniques, for example by employing blunt-ended or staggerended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (See, e.g., *Current Protocols in Molecular Biology*, Eds. Ausubel et al. John Wiley & Sons: 1992). Moreover, many expression vectors are commercially available that already encode a fusion moiety (e.g., a GST polypeptide). An isolated nucleotide encoding a transcriptionally regulated protein can be cloned into such an expression vector such that the fusion moiety is linked in-frame to the nucleotide.

Large amounts of the recombinant DNA molecules may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially *Escherichia coli* or *Saccharomyces cerevisiae*. Commonly used prokaryotic hosts include strains of *Escherichia coli*, although other prokaryotes, such as *Bacillus subtilis* or a pseudomonad, may also be used. Eukaryotic host cells include yeast, filamentous fungi, animal, plant, insect, amphibian and avian species. Such factors as ease of manipulation, ability to appropriately glycosylate expressed proteins, degree and control of protein expression, ease of purification of expressed proteins away from cellular contaminants or other factors influence the choice of the host cell.

As used herein, "recombinant host cells" are those which have been genetically modified to contain an isolated or other recombinant DNA molecule, as described herein. The DNA can be introduced by any means known to the art which is appropriate for the particular type of cell, including without limitation, transformation with plasmids, including different methods of plasmid delivery such as, without limitation, liposomal delivery, electroporation, or naked plasmid injection; transduction with viral vectors; or DNA delivery mediated by polymeric agents.

The present invention provides for cells and methods for obtaining cells that contain the nucleic acids of the invention, wherein the nucleic acid transcribes a nonsense mediated mRNA transcript which is translated into a transcriptionally regulated protein. The cells comprising the nucleic acids of the invention have improved control over the modulation of the dynamics of protein secretion. As used herein, the term "modulating protein secretion" is used interchangeably with the term "modulating secretion dynamics," and refers to a statistically significant effect on the levels of protein secretion due to the introduction of the heterologous nucleic acid transcribing a nonsense mediated mRNA transcript in comparison to the levels of protein secretion upon introduction of a heterologous nucleic acid that does not transcribe a nonsense mediated mRNA transcript. In a preferred embodiment, the introduction of the heterologous nucleic acid of the invention leads to a faster down-regulation of the secretion of the protein of interest. Preferably, the acceleration of the down-regulation of the secretion of the protein is due to increased degradation of the mRNA transcript encoding the transcriptionally regulated protein due to nonsense mediated mRNA decay. Methods to determine levels of protein secretion are well known to those of ordinary skill in the art.

In addition to fragments and fusion polypeptides of the transcriptionally regulated proteins described herein, the present invention includes homologs and analogs of naturally occurring transcriptionally regulated proteins and nucleotides encoding transcriptionally regulated proteins, and of naturally occurring nucleotides encoding a transcriptionally regulated protein. "Homologs" are defined herein as two nucleic acids or polypeptides that have similar, or substantially identical, nucleotide or amino acid sequences, respectively. Homologs include allelic variants, orthologs, paralogs, agonists and antagonists of transcriptionally regulated proteins as defined hereafter. The term "homolog" further encompasses nucleic acid molecules that differ due to degeneracy of the genetic code and thus encode the same transcriptionally regulated protein molecule. As used herein a "naturally occurring" transcriptionally regulated protein refers to a transcriptionally regulated protein amino acid sequence that occurs in nature. Similarly, a "naturally occurring" isolated nucleotide encoding a transcriptionally regulated protein refers to a nucleic acid sequence that occurs in nature.

Nucleic acid molecules corresponding to natural allelic variants and analogs, orthologs and paralogs of a transcriptionally regulated protein or isolated nucleotide encoding a transcriptionally regulated protein can be isolated using a hybridization probe according to standard hybridization techniques under stringent or moderate hybridization conditions. In an alternative embodiment, homologs can be identified by screening combinatorial libraries of mutants, for agonist or antagonist activity. There are a variety of methods that can be used to produce libraries of potential transcriptionally regulated protein homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential transcriptionally regulated protein sequences. Methods for synthesizing degenerate oligonucleotides are known in the art. See, e.g., Narang, S. A., 1983, *Tetrahedron* 39:3; Itakura et al., 1984, *Annu. Rev. Biochem.* 53:323; Itakura et al., 1984, *Science* 198:1056; Ike et al., 1983, *Nucleic Acid Res.* 11:477.

In addition, libraries of fragments of the transcriptionally regulated protein coding regions can be used to generate a variegated population of transcriptionally regulated protein fragments for screening and subsequent selection of homologs of a transcriptionally regulated protein. In one embodiment, a library of coding sequence fragments can be generated by treating a double stranded PCR fragment of a transcriptionally regulated protein coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the transcriptionally regulated protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of transcriptionally regulated protein homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify transcriptionally regulated protein homologs (Arkin & Yourvan, 1992, *PNAS* 89:7811-7815; Delgrave et al., 1993, *Polypeptide Engineering* 6(3):327-331).

As stated above, the present invention includes transcriptionally regulated proteins, nucleic acids encoding transcriptionally regulated proteins and homologs and analogs thereof. To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 25-30%, preferably at least 30-40%, and more preferably at least about 40-50%, 50-60%, 60-70%, 70-75%, 75-80%, 80-85%, 85-90% or 90-95%, and most preferably at least about 96%, 97%, 98%, 99% or more identical to an entire amino acid sequence. In yet another embodiment, the isolated amino acid homologs included in the present invention are at least about 25-30%, preferably at least 40-50%, and more preferably at least about 50-60%, 60-70%, 70-75%,75-80%,80-85%, 85-90% or 90-95%, and most preferably at least about 96%,97%, 98%, 99% or more identical to an entire amino acid sequence encoded by a nucleic acid sequence. In other embodiments, the transcriptionally regulated protein amino acid homologs have sequence identity over at least 15 contiguous amino acid residues, more preferably at least 25 contiguous amino acid residues, and most preferably at least 35 contiguous amino acid residues.

For the purposes of the invention, the percent sequence identity between two nucleic acid or polypeptide sequences may be determined using the "Blast Two Sequences" program available at National Center for Biotechnology Information (http://www.ncbi.nlm.nih.gov/blast/bl2seq/bl2.html). The percent sequence identity of two nucleic acids is determined using the algorithm of Karlin & Altschul, 1990 Proc. Natl. Acad. Sci. USA 87:2264-2268, modified as in Karlin & Altschul, 1993 Proc. Natl. Acad. Sci. USA 90:5873-5877. Such an algorithm is incorporated into the NBLAST and XBLAST programs of Altschul et al., 1990 J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al., 1997 Nucl. Acids. Res. 25:3389-3402. When utilizing BLAST and Gapped BLAST programs, the default parameters of the respective programs (NBLAST and XBLAST) are used. See http://www.ncbi.nih.gov/. It is to be understood that for the purposes of determining sequence identity when comparing a DNA sequence to an RNA sequence, a thymidine nucleotide is equivalent to a uracil nucleotide.

Hybridization procedures are useful for identifying polynucleotides with sufficient homology to the subject regulatory sequences to be useful as taught herein. The particular hybridization technique is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

Various degrees of stringency of hybridization can be employed for studies of cloned sequences isolated as described herein. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example in Keller, G. H., M. M. Manak, 1987 *DNA Probes*, Stockton Press, New York, N.Y., pp. 169-170, hereby incorporated by reference. In a preferred embodiment, the hybridization is selective for target DNA. As used herein, the term "selective hybridization" or "selectively hybridizing" refers to the ability to discern between the binding of a nucleic acid sequence to a target DNA sequence as compared to other non-target DNA sequences.

As used herein, moderate to high stringency conditions for hybridization are conditions that achieve the same, or about the same, degree of specificity of hybridization as the conditions described herein. As used herein, the term "highly stringent" or "high stringency conditions" comprises hybridizing at 68° C. in 5× SSC/5× Denhardt's solution/0.1% SDS, and washing in 0.2× SSC/0.1% SDS at 65° C. As used herein, the term "moderately stringent" or "moderate stringency conditions" comprise hybridizing at 55° C. in 5× SSC/5× Denhardt's solution/0.1% SDS and washing at 42° C. in 3× SSC. The parameters of temperature and salt concentration can be varied to achieve the desired level of sequence identity between probe and target nucleic acid. See, e.g., Sambrook et al. 1989 *Molecular Cloning*, Second Edition, Cold Spring Harbor Laboratory, Plainview, N.Y. Ausubel et al., 1995 *Current Protocols in Molecular Biology*, John Wiley & Sons, NY, N.Y., Meinkoth and Wahl, 1984, *Anal. Biochem.* 138:267-284; or Tijssen, 1993, *Laboratory Techniques in Biochemistry and Molecular Biology: Hybridization with Nucleic Acid Probes*, Part I, Chapter 2, Elsevier, N.Y., for further guidance on hybridization conditions.

Specifically, hybridization of immobilized DNA in Southern blots with $^{32}$P-labeled gene specific probes is performed by standard methods (Maniatis et al., 1982 *Molecular Cloning*, Cold Spring Harbor Laboratory, Plainview, N.Y.). As used herein, a "probe" is typically attached to a label or reporter molecule and is used to identify and isolate other sequences of interest. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction. e.g., by the phosphoramidite method described by Beaucage & Caruthers, 1981 Tetra. Letts. 22: 1859-1862 or the triester method according to Matteuci et al., 1981 J. Am. Chem. Soc., 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

In general, hybridization and subsequent washes are carried out under moderate to high stringency conditions that allowed for detection of target sequences with homology to a particular nucleic acid molecule of interest. For double-stranded DNA gene probes, hybridization can be carried out overnight at 20-25° C. below the melting temperature (Tm) of the DNA hybrid in 6×SSPE 5×Denhardt's solution, 0.1% SDS, 0.1 mg/ml denatured DNA. The melting temperature is described by the following formula (Beltz et al., 1983 *Methods of Enzymology*, R. Wu, L, Grossman and K Moldave (Eds.) Academic Press, New York 100:266-285).

$$Tm=81.5° C.+16.6 \text{ Log}[Na^+]+0.41(\%G+C)-0.61(\% \text{ formamide})-600/\text{length of duplex in base pairs}.$$

Washes are typically carried out as follows: twice at room temperature for 15 minutes in 1×SSPE, 0.1% SDS (low stringency wash), and once at TM-20° C. for 15 minutes in 0.2×SSPE, 0.1% SDS (moderate stringency wash).

For oligonucleotide probes, hybridization is carried out overnight at 10-20° C. below the melting temperature (Tm) of the hybrid 6× SSPE, 5× Denhardt's solution, 0.1% SDS, 0.1 mg/ml denatured DNA. Tm for oligonucleotide probes is determined by the following formula: TM(° C.)=2(number T/A base pairs+4(number G/C base pairs) (Suggs et al., 1981 *ICB-UCLA Symp. Dev. Biol. Using Purified Genes*, D. D. Brown (Ed.), Academic Press, New York, 23:683-693).

Washes are typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used: Low, 1 or 2× SSPE, room temperature; Low, 1 or 2×SSPE, 42° C.; Moderate, 0.5× or 1×SSPE, 60° C.; and High, 0.1×SSPE, 65° C.

One subset of these homologs are allelic variants. As used herein, the term "allelic variant" refers to a nucleotide sequence containing polymorphisms that lead to changes in the amino acid sequences of a transcriptionally regulated protein and that exist within a natural population. Such natural allelic variations can typically result in 1-5% variance in a transcriptionally regulated protein or isolated nucleotide encoding a transcriptionally regulated protein. Allelic variants can be identified by sequencing the nucleic acid sequence of interest in a number of different plants, or other organisms, which can be readily carried out by using hybridization probes to identify the same transcriptionally regulated protein or isolated nucleotide encoding a transcriptionally regulated protein genetic locus in those organisms. Any and all such nucleic acid variations and resulting amino acid polymorphisms or variations in a transcriptionally regulated protein or isolated nucleotide encoding a transcriptionally regulated protein that are the result of natural allelic variation and that do not alter the functional activity of a transcriptionally regulated protein or isolated nucleotide encoding a transcriptionally regulated protein, are intended to be within the scope of the invention.

Moreover, nucleic acid molecules encoding transcriptionally regulated proteins from the same or other species such as analogs, orthologs, and paralogs, are intended to be within the scope of the present invention. As used herein, the term "analogs" refers to two nucleic acid sequences that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, *Science* 278(5338):631-637). Analogs, orthologs and paralogs of a naturally occurring transcriptionally regulated protein can differ from the naturally occurring transcriptionally regulated protein by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98% or even 99% identity or sequence identity with all or part of a naturally occurring transcriptionally regulated protein amino acid sequence and will exhibit a function similar to a transcriptionally regulated protein.

In addition to naturally-occurring variants of a transcriptionally regulated protein sequence that may exist in the population, the skilled artisan will further appreciate that changes can be introduced by mutation into a nucleotide sequence, thereby leading to changes in the amino acid sequence of the encoded transcriptionally regulated protein, without altering the functional activity of the transcriptionally regulated protein. For example, nucleotide substitutions leading to amino acid substitutions at "non-essential" amino acid residues can be made in a sequence. A "non-essential" amino acid residue is a residue that can be altered from the wild-type sequence of one of the transcriptionally regulated proteins without altering the activity of said transcriptionally regulated protein, whereas an "essential" amino acid residue is required for transcriptionally regulated protein activity. Other amino acid residues, however, (e.g., those that are not conserved or only semi-conserved in the domain having transcriptionally regulated protein activity) may not be essential for activity and thus are likely to be amenable to alteration without altering the activity.

An isolated nucleic acid molecule encoding a transcriptionally regulated protein can be created by introducing one or more nucleotide substitutions, additions or deletions into a nucleotide sequence, such that one or more amino acid substitutions, additions, or deletions are introduced into the encoded polypeptide. Mutations can be introduced into a nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a transcriptionally regulated protein is preferably replaced with another amino acid residue from the same side chain family. Alternatively, in another embodiment, mutations can be introduced randomly along all or part of a transcriptionally regulated protein coding sequence, such as by saturation mutagenesis, and the resultant mutants can be screened for a transcriptionally regulated protein activity described herein to identify mutants that retain transcriptionally regulated protein activity. Following mutagenesis, the encoded polypeptide can be expressed recombinantly and the activity of the polypeptide can be determined.

Additionally, optimized nucleic acids encoding transcriptionally regulated proteins can be created. As used herein, "optimized" refers to a nucleic acid that is genetically engineered to increase its expression in a given organism, to increase its activity in a given organism, to increase its secretion in a given organism. For example, to provide optimized nucleic acids, the DNA sequence of the gene can be modified to 1) comprise codons preferred by highly expressed genes; 2) comprise an A+T content in nucleotide base composition to that substantially found in the organism of interest; 3) form a initiation sequence; or 4) eliminate sequences that cause destabilization, inappropriate polyadenylation, degradation, and termination of RNA, or that form secondary structure hairpins or RNA splice sites.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1\ Z\ Xn-Yn\ Xn$ times $100\ Z$ where $Xn$=frequency of usage for codon n in the host cell; $Yn$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a nucleotide encoding a transcriptionally regulated protein can be optimized such that its distribution frequency of codon usage deviates, preferably, no more than 25% from that of highly expressed genes and, more preferably, no more than about 10%. In addition, consideration is given to the percentage G+C content of the degenerate third base. Optimized nucleic acids of this invention also preferably have CG and TA doublet avoidance indices closely approximating those of the chosen host. More preferably these indices deviate from that of the host by no more than about 10-15%.

In addition to the nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of a sequence; an anti-sense sequence; or naturally occurring mutants thereof. Primers based on a nucleotide sequence can be used in PCR reactions to clone transcriptionally regulated proteins and nucleotides encoding transcriptionally regulated protein homologs. Probes based on the nucleotides encoding transcriptionally regulated proteins can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a transcriptionally regulated protein, such as by measuring a level of a nucleotide encoding a transcriptionally regulated protein, in a sample of cells, e.g., detecting mRNA levels or determining whether a genomic gene has been mutated or deleted.

In alternative embodiments, the isolated nucleotide encoding a transcriptionally regulated protein comprises a nucleic acid sequence that hybridizes in 5× SSC at 55° C. to any of the polynucleotides as defined above. In other embodiments, the isolated nucleotide encoding a transcriptionally regulated protein is modified to include a promoter operatively linked to a foreign nucleic acid.

In particular, a useful method to ascertain the level of transcription of a gene (an indicator of the amount of mRNA available for translation to the gene product) is to perform a Northern blot. For reference, see, for example, Ausubel et al., 1988, Current Protocols in Molecular Biology, Wiley: New York The information from a Northern blot at least partially demonstrates the degree of transcription of the transformed gene. Total cellular RNA can be prepared from cells, tissues or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. See, for example, Ausubel et al., 1988, Current Protocols in Molecular Biology, Wiley: New York The invention further provides an isolated recombinant expression vector comprising an isolated nucleic acid encoding a transcriptionally regulated protein as described above, wherein expression of the vector in a host cell results in decreased stability of the mRNA encoding for the protein and/or decreased secretion of the protein compared to a wild-type variety of the host cell, or compared to a host cell that is expressing a vector comprising one copy of the isolated nucleotide encoding a transcriptionally regulated protein, wherein there are no supplementary nucleic acid sequences interposed between the stop codon of the portion of the mRNA transcript encoding for the transcriptionally regulated protein and the polyadenylation sequence. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors can include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, *Gene Expression Technology: Methods in Enzymology* 185, Academic Press, San Diego, Calif. (1990) and Gruber and Crosby, in: *Methods in Plant Molecular Biology and Biotechnology*, Eds. Glick and Thompson, Chapter 7, 89-108, CRC Press: Boca Raton, Fla., including the references therein. For appropriate enhancer and other expression control sequences, see also Enhancers and Eukaryotic Gene Expression, Cold Spring Harbor Press, N.Y. (1983). Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., transcriptionally regulated proteins, mutant forms of transcriptionally regulated proteins, fusion polypeptides, etc.).

The recombinant expression vectors of the invention can be designed for expression of transcriptionally regulated proteins in prokaryotic or eukaryotic cells. For example, genes encoding transcriptionally regulated proteins can be expressed in bacterial cells such as *C. glutamicum*, insect cells (using baculovirus expression vectors), yeast and other fungal cells (See Romanos, M. A. et al., 1992, *Foreign gene expression in Yeast: a Review, Yeast* 8:423-488; van den Hondel, C. A. M. J. J. et al., 1991, Heterologous gene expression in filamentous fungi, in: *More Gene Manipulations in Fungi*, J. W. Bennet & L. L. Lasure, Eds., p.396-428: Academic Press: San Diego; and van den Hondel, C. A. M. J. J. & Punt, P. J., 1991, *Gene transfer systems and vector development for filamentous fungi*, in: *Applied Molecular Genetics of Fungi*, Peberdy, J. F. et al., eds., p. 1-28, Cambridge University Press: Cambridge), algae (Falciatore et al., 1999, *Marine Biotechnology* 1(3):239-251), ciliates, multicellular plant cells (See Schmidt, R. and Willmitzer, L., 1988, *High efficiency Agrobacterium tumefaciens-mediated transformation of Arabidopsis thaliana leaf and cotyledon explants, Plant Cell Rep.* 583-586; *Plant Molecular Biology and Biotechnology*, C Press, Boca Raton, Fla., chapter 6/7, S.71-119 (1993); F. F. White, B. Jenes et al., *Techniques for Gene Transfer*, in: *Transgenic Plants*, Vol.1, Engineering and Utilization, Eds. Kung And R. Wu, 128-43, Academic Press: 1993; Potrykus, 1991, *Annu. Rev. Plant Physiol. Plant Molec. Biol.* 42:205-225 and references cited therein) or mammalian cells. In a preferred embodiment, the host cell is a mammalian cell, and more preferably, is a human cell. In one preferred embodiment, the human cell is a non-β cell. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL (New England Biolabs, Beverly, Mass.) and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the transcriptionally regulated protein is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant transcriptionally regulated proteins unfused to GST can be recovered by cleavage of the fusion polypeptide with thrombin.

Examples of suitable inducible non-fusion *E. coli* expression vectors include pTrc (Amann et al., 1988, Gene 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., *Gene Expression Technology: Methods in Enzymology* 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, *Nucleic Acids Res.* 20:2111-2118). Such alteration of nucleic acid sequences of the invention can be carried out by standard DNA synthesis techniques.

In another embodiment, the transcriptionally regulated protein expression vector is a yeast expression vector. Examples of vectors for expression in yeast *S. cerevisiae* include pYepSec1 (Baldari, et al., 1987, *EMBO J.* 6:229-234), pMFa (Kurjan and Herskowitz, 1982, *Cell* 30:933-943), pJRY88 (Schultz et al., 1987, *Gene* 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, *Gene transfer systems and vector development for filamentous fungi,* in: *Applied Molecular Genetics of Fungi,* J. F. Peberdy, et al., eds., p. 1-28, Cambridge University Press: Cambridge.

Alternatively, the transcriptionally regulated proteins of the invention can be expressed in insect cells using baculovirus expression vectors. Baculovirus vectors available for expression of polypeptides in cultured insect cells (e.g., Sf9 cells) include the pAc series (Smith et al., 1983, *Mol. Cell Biol.* 3:2156-2165) and the pVL series (Lucklow and Summers, 1989, *Virology* 170:31-39).

In yet another embodiment, a transcriptionally regulated protein nucleic acid of the invention is expressed in mammalian cells using a mammalian expression vector. Examples of mammalian expression vectors include pCDM8 (Seed, B., 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. *Molecular Cloning: A Laboratory Manual,* 2nd Ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto & Baltimore, 1989, *EMBO J.* 8:729-733) and immunoglobulins (Banerji et al., 1983, *Cell* 33:729-740; Queen & Baltimore, 1983, *Cell* 33:741-748), neuron-specific promoters (e.g., the neurofilament promoter; Byrne & Ruddle, 1989, *PNAS* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel & Gruss, 1990, *Science* 249:374-379) and the fetopolypeptide promoter (Campes & Tilghman, 1989, *Genes Dev.* 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. As used herein, the term "selectable marker" refers to a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depent on the host cell; appropriate markers for different hosts are known in the art.

Other suitable methods for transforming or transfecting host cells can be found in Sambrook, et al., *Molecular Cloning: A Laboratory Manual*. 2nd Ed., Cold Spring Harbor Laboratory, Cold Spring Harbor Laboratory Press, Cold Spring Harbor, N.Y., 1989, and other laboratory manuals.

In another embodiment, recombinant organisms can be produced that contain selected systems which allow for regulated expression of the introduced gene. For example, inclusion of a gene encoding a transcriptionally regulated protein on a vector placing it under control of the lac operon permits expression of the gene encoding a transcriptionally regulated protein only in the presence of IPTG. Such regulatory systems are well known in the art.

Gene expression should be operatively linked to an appropriate promoter conferring gene expression in a timely, cell or tissue specific manner. Promoters useful in the expression cassettes of the invention include any promoter that is capable of initiating transcription in a cell.

The promoter may be constitutive, inducible, developmental stage-preferred, cell type-preferred, tissue-preferred, or organ-preferred. Constitutive promoters are active under most conditons. Examples of constitutive promoters include the CaMV 19S and 35S promoters (Odell et al., 1985, *Nature* 313:810-812), the sX CaMV 35S promoter (Kay et al., 1987, *Science* 236:1299-1302) the Sep1 promoter, the ubiquitin promoter (Christensen et al., 1989, *Plant Molec Biol* 18:675-689); pEmu (Last et al., 1991, *Theor. Appl. Genet.* 81:581-588), and the like.

Inducible promoters are active under certain environmental conditions, such as the presence or absence of a nutrient or metabolite, heat or cold, light, pathogen attack, anaerobic conditons, and the like. Chemically inducible promoters are especially suitable if gene expression is wanted to occur in a time specific manner. Developmental stage-preferred promoters are preferentially expressed at certain stages of development. Additional flexibility in controlling heterologous gene expression may be obtained by using DNA binding domains and response elements from heterologous sources (i.e., DNA binding domains from non-mammalian sources).

Another aspect of the invention pertains to host cells into which a heterologous nucleic acid of the invention has been introduced. The terms "host cell" and "recombinant host cell" are used interchangeably herein. It is understood that such terms refer not only to the particular subject cell but they also apply to the progeny or potential progeny of such a cell. As such, both the original host cell that contains the heterologous nucleic acid of the invention and any progeny cells are transgenic. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a transcriptionally regulated protein can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Similarly, a isolated nucleotide encoding a transcriptionally regulated protein can be introduced into any prokaryotic or eukaryotic cell, such as bacterial cells, insect cells, fungal cells, or mammalian cells, algae, ciliates, plant cells, fungi, or other microorganisms. In preferred embodiments, the host cell is a mammalian cell. In other preferred embodiments, the host cell is a non-β cell. In other preferred embodiments, the host cell is a hepatic cell. In a particularly preferred embodiment, the host cell is a human hepatic cell. In other preferred embodiments, the host cell is an autologous cell. In other preferred embodiments, the host cell is an immortalized cell line. Preferred immortalized cell line include hepatic cell lines, and in particular, the human HepG2 cell line. Other suitable host cells and cell lines are known to those skilled in the art. Because routine errors of gene expression due to premature termination of translation are inevitable and truncated proteins generated by nonsense mutant mRNAs are potentially toxic to cells, it is expected that all the mammalian cells have evolved to recognize mRNAs containing premature termination codons and host nonsense mediated mRNA decay. Specifically, NMD has been demonstrated in lymphoblasts (Rajavel, K. S. & Neufeld, E. F. 2001, Mol. Cell Biol. 21:5512-9), fibroblasts (Zhang, J., et al. 1998, Mol. Cell Biol. 18:5272-83), chondrocytes (Bateman, J. F., et al. 2003, Hum. Mol. Genet. 12:217-25), and Chinese hamster ovary (CHO) cells (Kessler, O. & Chasin, L. A. 1996, Mol. Cell Biol. 16:4426-35), among others. Thus, any host cell or cell line that recognize premature termination codons and responds by inducing nonsense mediated mRNA decay are candidates for the application of the invention described herein.

A host cell of the invention, such as a eukaryotic host cell in culture, can be used to produce (i.e., express) a transcriptionally regulated protein. Accordingly, the invention further provides methods for producing transcriptionally regulated proteins using the host cells of the invention. In one embodiment, the method comprises culturing the host cell of invention (into which a recombinant expression vector encoding a transcriptionally regulated protein has been introduced, or into which genome has been introduced a gene encoding a wild-type or altered transcriptionally regulated protein) in a suitable medium until transcriptionally regulated protein is produced. In another embodiment, the method encompasses the introduction of a heterologous isolated nucleotide encoding a transcriptionally regulated protein, resulting in a down-regulation in secretion of the transcriptionally regulated protein.

A host cell of the invention, such as a eukaryotic host cell in culture, can be used to treat a patient in need thereof, comprising administering to the patient a therapeutically effective amount of the cell. In a preferred embodiment, the cell comprises a heterologous nucleic acid comprising a preproinsulin encoding nucleic acid. In a preferred embodiment, the nucleic acid encodes human insulin. In a preferred embodiment, the patient treated with the host cell of the invention has diabetes. In a further preferred embodiment, the disease is insulin-dependent diabetes.

Standard techniques for cloning, DNA isolation, amplification and purification, for enzymatic reactions involving DNA ligase, DNA polymerase, restriction endonucleases and the like, various separation techniques, and techniques to analyze mRNA and proteins are those known and commonly employed by those skilled in the art. A number of standard techniques are described in Sambrook et al:, 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y; Wu (Ed.) 1993 Meth. Enzymol. 218, Part I; Wu (ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames & Higgins (Eds.) 1985 Nucleic Acid Hybridization, IRL Press, Oxford, UK; and Setlow & Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

EXAMPLES

Example 1

PPI mRNA Engineering and Expression

Plasmids for Insulin Expression

Vectors A-E in FIG. 1 are five plasmids constructed to systematically increase insulin expression in HepG2 cells. Wild-type human preproinsulin cDNA, furin-compatible with furin cleavage sites at the B-C and C-A junctions, and furin-compatible with His B10-to-Asp mutation (B10 mutation) were all generous gifts from Genentech, Inc (San Francisco, Calif.; see Groskreutz, et al., C. M., 1994, J. Biol. Chem. 269:6241-5). The backbone of the insulin expression plasmids originated from an 1822 bp BglII/BamHI fragment of plasmid pRL/Null (Promega, Madison, Wis.). A 508 bp XbaI/BamHI restriction fragment containing both the Simian Virus 40 (SV40) late polyadenylation and SV40 enhancer signals from plasmid pGL3-control (Promega) was used to replace the SV40 late polyadenylation signal in pRL/Null to prepare the plasmid with the SV40 enhancer. The human cytomegalovirus (CMV) promoter used to drive the insulin gene expression was obtained from an 883 bp BglII/NheI restriction fragment of plasmid pcDNA3.1 (+) (Invitrogen, Carlsbad, Calif.). The CMV promoter was connected to the BglII and SpeI sites of pRL/Null to prepare the plasmid with an intron, or to the BglII and NheI sites to prepare the plasmid without an intron. Different versions of XbaI/XbaI preproinsulin cDNA fragment were connected to the backbones using NheI and XbaI sites.

The intron connected to the 5' of preproinsulin gene was the 13 7-bp chimeric intron from the backbone plasmid pRL/Null (Promega, Madison, Wis.), having the sequence 5'-CAGGTAAGTATCAAGGTTACAAGACAG-GTTTAAGGAGACCAATAGAAACTGGGCTT GTC-GAGACAGAGAAGACTCTTGCGTTTCT-GATAGGCACCTATTGGTCTTACTGACAT CCACTTTGCCTTTCTCTCCACAGG-3' (SEQ ID NO:1). The chimeric intron is included in the insulin expression cassette for optimal splicing since studies have demonstrated that splicing is important for mRNA transport across the nucleus membrane (Luo, M.-J. & Reed, R., 1999 Proc. Natl. Acad. Sci. USA, 96: 14937-42) and the incorporation of an intron in an expression cassette can improve the levels of recombinant gene expression (Huang, M. T. & Gorman, C. M., 1990 Nucleic Acids Res. 18:937-47).

The backbone of the Tet-responsive insulin expression plasmid was obtained from a 2074 bp XhoI/XbaI fragment of plasmid pRL/Null (Promega). The tetracycline-responsive promoter was obtained from a 448 bp XhoI/EcoRI restriction fragment of plasmid pTRE2pur (Clontech, Palo Alto, Calif.). This promoter was inserted into the multiple cloning sites of pRL/Null. For the control plasmid containing one copy of insulin gene, a 360 bp XbaI/XbaI restriction fragment containing the furin-compatible insulin gene with B10 mutation was connected to the backbone using NheI and XbaI sites (vector F). For the engineered plasmid, two additional copies of the insulin gene were consecutively inserted to the backbone via the XbaI site with the same head-tail configuration (vector G). After transcription, the engineered PPI mRNA contained three consecutive copies of the insulin gene with stop codons in the middle of the transcript. Translation is expected to stop in the middle of the engineered PPI mRNA and induce NMD. The XhoI/XhoI restriction fragments of the Clontech plasmids cat# K1620-A and K1621-A were used to prepare plasmids pTet-Off and pTet-On, respectively.

The sequence of the His B10-to-Asp mutated human PPI cDNA with furin cleavage sites at the B-C and C-A junctions is 5'- ATGGCCCTGTGGATGCGCCTCCTGC-CCCTGCTG GCGCTGCTGGCCCTCTGGGGACCT-GACCCAGCCGCAGCCTTTGTGAACCAACACCTG TGCGGATCCGACCTGGTGGAAGCTCTC-TACCTAGTGTGCGGGGAACGAGGCTTCTTC TACA-CACCCAGGACCAAGCGGGAGGCAGAG-GACCTGCAGGTGGGGCAGGTGGAGC TGGGCGGGGGCCCTGGTGCAGGCAGCCT-GCAGCCCTTGGCCCTGGAGGGATCCCGG CAGAAGCGTGGCATTGTGGAACAATGCT-GTACCAGCATCTGCTCCCTCTACCAGCTG GAGAACTACTGCAACTAG-3' (SEQ ID NO:2). The sequence of the three copies of the His B10-to-Asp mutated human PPI cDNA with furin cleavage sites at the B-C and C-A junctions is 5'-CTAGAGTCGACCTGCAGAAGCT-TACCATGGCCCTGTGGATGCGCCTCCTGCCCCTG CTGGCGCTGCTGGCCCTCTGGGGACCT-GACCCAGCCGCAGCCTTTGTGAACCAACA CCTGT-GCGGATCCGACCTGGTGGAAGCTCTC-TACCTAGTGTGCGGGGAACGAGGC TTCTTCTACACACCCAGGACCAAGCGG-GAGGCAGAGGACCTGCAGGTGGGGCAGG TGGAGCTGGGCGGGGGCCCTGGTGCAG-GCAGCCTGCAGCCCTTGGCCCTGGAGGG ATCCCG-GCAGAAGCGTGGCATTGTGGAACAAT-GCTGTACCAGCATCTGCTCCCTCT ACCAGCTGGAGAACTACTGCAAC-TAGTCTAGAGTCGACCTGCAGAAGCTTACCAT GGCCCTGTGGATGCGCCTCCTGCCCCT-GCTGGCGCTGCTGGCCCTCTGGGGACCTG ACCCAGCCGCAGCCTTTGTGAACCAA-
CACCTGTGCGGATCCGACCTGGTGGAAGC TCTC-
TACCTAGTGTGCGGGGAACGAGGCTTCT-
TCTACACACCCAGGACCAAGCGG
GAGGCAGAGGACCTGCAGGTGGGGCAG-
GTGGAGCTGGGCGGGGGCCCTGGTGCA GGCAGC-
CTGCAGCCCTTGGCCCTGGAGGGATC-
CCGGCAGAAGCGTGGCATTGTGG
AACAATGCTGTACCAGCATCTGCTC-
CCTCTACCAGCTGGAGAACTACTGCAACTAG
AGTCGACCTGCAGAAGCTTACCATGGC-
CCTGTGGATGCGCCTCCTGCCCCTGCTGG CGCT-
GCTGGCCCTCTGGGGACCTGACCCAGC-
CGCAGCCTTTGTGAACCAACACCTG
TGCGGATCCGACCTGGTGGAAGCTCTC-
TACCTAGTGTGCGGGGAACGAGGCTTCTT CTACA-
CACCCAGGACCAAGCGGGAGGCAGAG-
GACCTGCAGGTGGGGCAGGTGGA
GCTGGGCGGGGGCCCTGGTGCAGGCAGC-
CTGCAGCCCTTGGCCCTGGAGGGATCC CGGCA-
GAAGCGTGGCATTGTGGAACAATGCTG-
TACCAGCATCTGCTCCCTCTACC
AGCTGGAGAACTACTGCAACTAGTCTAGA-3' (SEQ
ID NO:3).

The sequence of the intron plus three copies of the mutated human insulin as described above is 5'CAGG-
TAAGTATCAAGGTTACAAGACAGGTT-
TAAGGAGACCAAT AGAAACTGGGCTTGTCGAGA-
CAGAGAAGACTCTTGCGTTTCTGATAGGCACCTAT
TGGTCTTACTGACATCCACTTTGC-
CTTTCTCTCCACAGGCTAGAGTCGACCTGCAG
AAGCTTACCATGGCCCTGTGGATGCGC-
CTCCTGCCCCTGCTGGCGCTGCTGGCCCT CTGGG-
GACCTGACCCAGCCGCAGCCTTTGT-
GAACCAACACCTGTGCGGATCCGACC
TGGTGGAAGCTCTCTACCTAGTGT-
GCGGGGAACGAGGCTTCTTCTACACACCCAGG
ACCAAGCGGGAGGCAGAGGACCTGCAG-
GTGGGGCAGGTGGAGCTGGGCGGGGC CCTGGT-
GCAGGCAGCCTGCAGCCCTTGGCCCTG-
GAGGGATCCCGGCAGAAGCGTG
GCATTGTGGAACAATGCTGTACCAG-
CATCTGCTCCCTCTACCAGCTGGAGAACTAC
TGCAACTAGTCTAGAGTCGACCTGCA-
GAAGCTTACCATGGCCCTGTGGATGCGCCT CCTGC-
CCCTGCTGGCGCTGCTGGCCCTCTGGG-
GACCTGACCCAGCCGCAGCCTTTG
TGAACCAACACCTGTGCGGATCCGAC-
CTGGTGGAAGCTCTCTACCTAGTGTGCGGG GAAC-
GAGGCTTCTTCTACACACCCAGGAC-
CAAGCGGGAGGCAGAGGACCTGCAGG
TGGGGCAGGTGGAGCTGGGCGGGGC-
CCTGGTGCAGGCAGCCTGCAGCCCTTGGC CCTG-
GAGGGATCCCGGCAGAAGCGTGGCAT-
TGTGGAACAATGCTGTACCAGCATC
TGCTCCCTCTACCAGCTGGAGAACTACT-
GCAACTAGAGTCGACCTGCAGAAGCTTA CCATG-
GCCCTGTGGATGCGCCTCCTGCCCCT-
GCTGGCGCTGCTGGCCCTCTGGGGA
CCTGACCCAGCCGCAGCCTTTGTGAAC-
CAACACCTGTGCGGATCCGACCTGGTGGA
AGCTCTCTACCTAGTGTGCGGGGAAC-
GAGGCTTCTTCTACACACCCAGGACCAAGC
GGGAGGCAGAGGACCTGCAG-
GTGGGGCAGGTGGAGCTGGGCGGGGGCCCTGGTG
CAGGCAGCCTGCAGCCCTTGGCCCTG-
GAGGGATCCCGGCAGAAGCGTGGCATTGT GGAA-
CAATGCTGTACCAGCATCTGCTCCCTC-
TACCAGCTGGAGAACTACTGCAACT AGTCTAGA-3'
(SEQ ID NO:4).

The amino acid sequence corresponding to the mutated human preproinsulin as defined in SEQ ID NO:2 is Met-ala-leu-trp-met-arg-leu-leu-pro-leu-leu-ala-leu-leu-ala-leu-trp-gly-pro-asp-pro-ala-ala-ala-phe-val-asn-gln-his-leu-cys-gly-ser-asp-leu-val-glu-ala-leu-tyr-leu-val-cys-gly-glu-arg-gly-phe-phe-tyr-thr-pro-arg-thr-lys-arg-glu-ala-glu-asp-leu-gln-val-gly-gln-val-glu-leu-gly-gly-gly-pro-gly-ala-gly-ser-leu-gln-pro-leu-ala-leu-glu-gly-ser-arg-gln-lys-arg-gly-ile-val-glu-gln-cys-cys-thr-ser-ile-cys-ser-leu-tyr-gln-leu-glu-asn-tyr-cys-asn-* (SEQ ID NO:5). The asterisk (*) indicates the presence of a termination codon. The underlined amino acid residues indicate the positions of mutation in comparison to wild-type human preproinsulin. The nucleic acid sequences and amino acid sequences for preproinsulin and insulin of other animal species, and variants within a species such as human, are well-known and publicly available.

Cell Culture and Transfection

HepG2 human hepatoma cells (ATCC, Manassas, Va.) were grown in DMEM supplemented with 10% fetal bovine serum, 1.1 mg/ml sodium pyruvate and 100 units/ml penicillin/streptomycin at 37° C. in a 5% CO2/95% air humidified atmosphere. Approximately $10^6$ cells were seeded in each 9.6 $cm^2$ well of 6-well plates and were fed with 2 ml culture medium for 8-12 hours prior to transfection. All transfections were carried out with FUGENE 6 reagent (Roche, Indianapolis, Ind.) following the manufacturer's directions. For each well, HepG2 cells were transfected for 24 hours with the plasmid DNA cocktail (2.1 μg or 2.25 μg) and 6 PI of FUGENE 6 reagent. Unless otherwise specified, transfected cells were incubated in culture medium for another 24-36 hours for recovery. Cells were then washed and incubated with culture medium for two consecutive 1-hour periods to stabilize insulin secretion before any tests were performed.

Systematic Increase of Insulin Expression

HepG2 cells were transiently transfected using 2 μg of test plasmid (FIG. 1, vector A, B, C, D or E) and 0.1 μg of plasmid pGL3-Control (Promega) for luciferase expression as internal standard. Cells were then incubated for 1 hour in culture medium, which was collected to assay for secreted insulin. Cells were detached using 2.5 ml 0.25% trypsin solution supplemented with 5 mg of collagenase type II for luciferase assay and cell counting.

Assay

Firefly luciferase activity from the internal control vector pGL3-Control was measured using the luciferase assay system (Promega) following the manufacturer's protocol and using an LS 5000 scintillation counter (Beckman, Fullerton, Calif.). Secreted insulin was measured by human insulin specific radioimmunoassay (RIA) kit (LINCO Research, St. Charles, Mich.). The primary antibody in the kit cross-reacts with proinsulin at less than 0.2%. Radioactivities were determined in Auto-Gamma Counting System, Cobra II (Packard, Meriden, Conn.).

The change of intracellular PPI mRNA level was quantified by the TaqMan real-time PCR technique (Applied Biosystems, Foster City, Calif.). Total RNA was isolated using RNeasy Mini Kit (Qiagen, Valencia, Calif.); cDNA was then synthesized using the Avian myoblastosis virus (AMV) Reverse Transcriptase Kit (Promega) to prepare templates for TaqMan real-time PCR.

The expression levels of PPI mRNA and of the internal reference tTA (tetracycline-reponsive transcriptional activator from co-transfected plasmid pTet-Off) mRNA were measured using probes labeled with 6FAM™ and VIC™ (Applied Biosystems), respectively, in separate tubes. The primers and probes (Table 1) were designed using Primer Express software (Applied Biosystems). Measuring preproinsulin mRNA-FAM and tTA mRNA-VIC permitted correction of discrepancies from differences in sample preparation and transfection efficiencies. PCR reactions were performed with the TaqMan Universal PCR Master Mix and the ABI PRISM 7700 Sequence Detection System (Applied Biosystems) using the following thermal cycle routine: 50° C. for 2 minutes 95° C. for 10 minutes, and then 40 cycles of 95° C. for 15 seconds, followed by 60° C. for 1 minute. A comparative threshold cycle (CT) method (User Bulletin Number 2; Applied Biosystems) was used to determine relative gene expression. Relative quantification of PPI mRNA was done by normalizing the PPI mRNA with the tTA mRNA signal and by assigning a value of 100 to the normalized sample level at time zero.

and a 20.7±3.8-fold higher insulin secretion rate in the absence relative to the presence of DOX. With the engineered plasmid, the corresponding values were 20.7±3.9-fold higher mRNA and 19.2±4.8-fold higher insulin secretion rate in the absence vs. presence of DOX.

NMD improved the secretory response of HepG2 cells but also reduced intracellular PPI mRNA levels and thus decreased insulin expression. To ameliorate this problem, insulin expression was increased before applying NMD. HepG2 hepatomas transiently transfected with vector D (FIG. 1) secreted insulin at a rate of 720 fmole/(hr·$10^6$ cells), which is higher than the basal insulin secretion rate of 380 fmole/(hr·$10^6$ cells) exhibited by βTC-3 mouse insulinomas (Mukundan, et al., 1995, Biochem. Biophys. Res. Commun. 210: 113-8). For Tet-responsive insulin expression, although the SV40 enhancer was not applied, the insulin secretion from Tet-Off transfected HepG2 cells in DOX-free medium was 320 fmole/(hr-106 cells) and 109 fmole/(hr·$10^6$ cells) when the control and engineered PPI mRNA, respectively, were used.

TABLE 1

Probe and primer sequences for TaqMan real-time PCR technique.

| Gene | Probe and primer sequence (5' → 3') | |
|---|---|---|
| Insulin | FAM probe: TCCGACCTGGTGGAAGCTCTCTACCTAGTG | (SEQ ID NO:6) |
| | Forward: TTTGTGAACCAACACCTGTGC | (SEQ ID NO:7) |
| | Reverse: GGGTGTGTAGAAGAAGCCTCGTT | (SEQ ID NO:8) |
| tTA | VIC probe: CCCGTAAACTCGCCCAGAAGCTAGGTGT | (SEQ ID NO:9) |
| | Forward: GGTCGGAATCGAAGGTTTAACA | (SEQ ID NO:10) |
| | Reverse: TGCCAATACAATGTAGGCTGCT | (SEQ ID NO:11) |

Results

Figure 2:
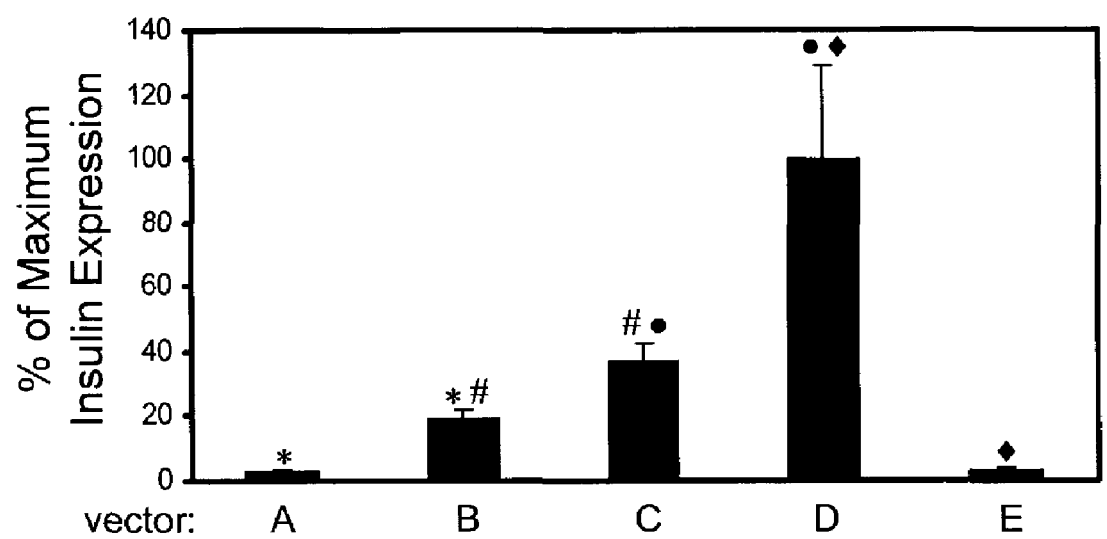
FIG. 2 demonstrates the systematic increase of insulin expression from transfected human HepG2 hepatomas. Cells were transiently co-transfected with the test vector shown in FIG. 1 (A, B, C, D or E) and the internal control plasmid pGL3-control. Luciferase, expressed through pGL3-control, was used to normalize the insulin secretion rate and thus correct for variations in transfection efficiency. The normalized insulin secretion rate from vector D (highest insulin expression vector) was assigned a value of 100. Experiments were performed in triplicate wells. *, # and ♦ indicate P values<0.02, and • indicates P value<0.04. P values were calculated using a one-tailed t-test, assuming unequal variances. Bars indicate standard deviation.

FIG. 1 shows the plasmids constructed to improve insulin expression. With the CMV promoter, vector D resulted in insulin secretion rates of 720±130 fmole/(hr·$10^6$ cells) from transiently transfected HepG2 hepatomas (FIG. 2). This was 32.0±9.4 fold higher than the secretion rate achieved with the furin-compatible insulin gene without any gene attachments (FIGS. 1 and 2, vector A), and 27.5±8.0 fold higher relative to the wild-type insulin gene with the chimeric intron and SV40 enhancer (FIGS. 1 and 2, vector E). However, because the SV40 enhancer is not compatible with the Tet-responsive system, vectors applied for Tet-responsive insulin expression did not contain this sequence, but they did contain the B-C and C-A junction and B10 His-to-Asp mutations, as well as the chimeric intron.

The control and engineered PPI mRNA expression plasmids (vectors F and G, FIG. 1) were each transiently co-transfected with plasmid pTet-Off in HepG2 cells. Use of the engineered PPI mRNA decreased the insulin expression level to 109±43 fmole/(hr·$10^6$ cells) from 320±55 fmole/(hr·$10^6$ cells) (n=4) of the control construct, or by 66%. Evidently, the decreased stability of engineered mRNA reduced intracellular mRNA levels and thus expression, as observed in many other nonsense mutations (Li, S. & Wilkinson, M. F., 1998, Immunity 8:135-41; Pulak, R. & Anderson, P., 1993, Genes. Dev. 7:1885-97). However, cells with both engineered and control plasmids were regulated in a similar fashion by DOX. With the control plasmid, transfected cells had a 24.8±5.2-fold higher mRNA expression Example 2

Dynamics of Insulin Expression and Secretion

Dynamic Insulin Expression

HepG2 cells were transiently co-transfected using 2 μg of plasmid pTet-Off (or pTet-On) and 0.25 μg of the control or engineered PPI mRNA expression plasmid (FIG. 1, vectors F, and G). Tet-Off transfected cells in parallel cultures were incubated in doxycycline (DOX)-free medium or in medium with 1 μg/ml DOX for 24-36 hours. Media were renewed, and cells were incubated for an additional 1 hour during which insulin secretion was measured; cells were then lysed for quantitative mRNA assay. To study the dynamics of insulin gene down-regulation, Tet-Off transfected cells were switched from DOX-free medium to 1 μg/ml DOX medium for 8 hours. Every hour, culture medium was renewed and collected for insulin assay. Every two hours, cells were lysed for quantitative mRNA assay. To dynamically regulate insulin secretion using Tet-On system, Tet-On transfected cells were switched from DOX-free medium to 1 μg/ml DOX medium for 1 hour, washed four-times, incubated with DOX-free medium for 7 hours, and the steps were repeated. Every hour, culture medium was renewed and collected for insulin assay.

Results

Figure 3:
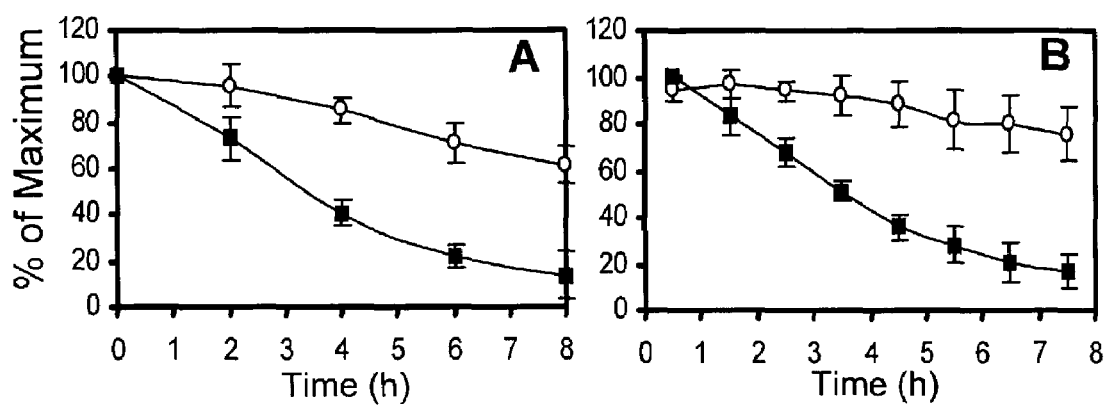
FIGS. 3A and B show the dynamics of down-regulation of insulin gene expression using the Tet-Off system with control (open circles) and engineered (filled squares) PPI mRNA expression.
FIG. 3B shows the down-regulation of insulin secretion rate. tTA (tetracycline-responsive transcriptional activator, from co-transfected plasmid pTet-Off, a component of the Tet-Off system) mRNA was used as an internal standard for quantitative PPI mRNA assay. In each independent test, the PPI mRNA was normalized by designating the sample without DOX treatment (t=0) as the calibrator and setting it at 100%; insulin secretion rates were normalized by designating the sample with the highest rate as the calibrator and setting it at 100%. After an 8-hour period of down-regulation, the control and the engineered PPI mRNA decreased to 61±8% (P<0.007) and 14±10% (P<0.003), respectively, and the insulin secretion rates to 75±12% (P<0.05) and 17±7% (P<0.002), respectively. Each experiment involved 3 independent tests. Bars indicate standard deviations.

The down-regulation of insulin gene expression was tested using the Tet-Off expression system. In the dynamic test, transcription was down-regulated by exposing cells at time zero to culture medium with 1 μg/ml DOX (FIG. 3). The engineered PPI mRNA exhibited a faster decline with a half-life of less than 4 hours relative to the control that had a half-life of more than 8 hours. The decline of insulin secretion rate followed the similar trends. Thus, immunoreactive insulin can be synthesized from the engineered PPI mRNA, and that the dynamics of down-regulation upon switching off transcription at both the mRNA and secreted protein levels are faster with the engineered PPI mRNA relative to control.

Figure 4:
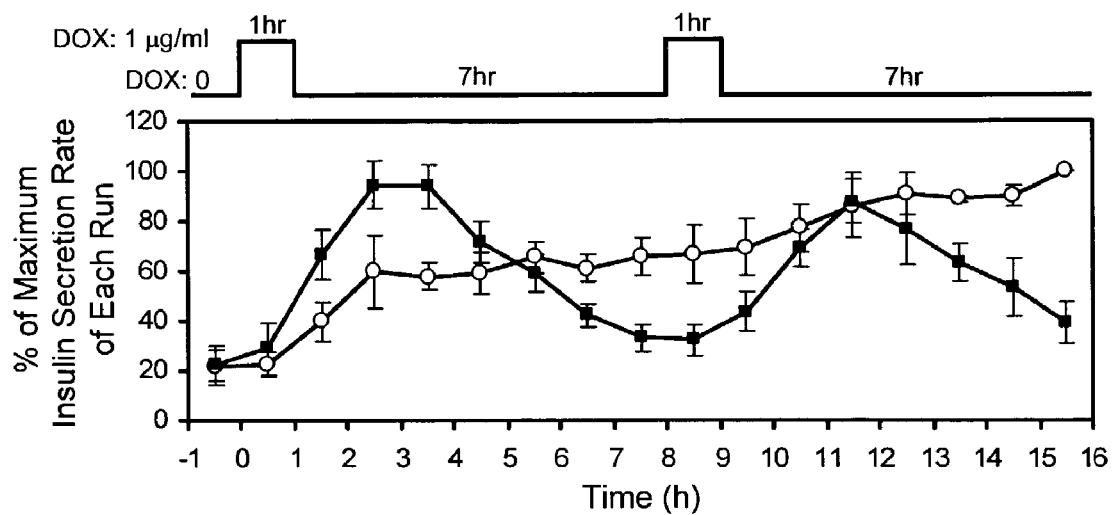
FIG. 4 shows the regulation of insulin secretion from transfected HepG2 cells using the Tet-On system with control (open circles) and engineered (filled squares) PPI mRNA expression. In each independent test, the insulin secretion rates were normalized by designating the sample with the highest rate as the calibrator and setting it at 100%. Each experiment involved 3 independent tests. Bars indicate standard deviations.

Up- and down-regulation of insulin secretion from transfected HepG2 cells was tested using the Tet-On system, in which DOX induces insulin gene expression. Using 1 hour of induction in an 8-hour cycle, insulin production from the engineered PPI mRNA responded to the transcriptional switches (FIG. 4). On the other hand, insulin production from the control PPI mRNA failed to decline during the 7-hour basal periods of exposure to DOX-free medium.

The specificity of the Tet-Off system and the sub-toxic DOX concentration used in this study (Gossen, et al., 1995, Science 268:1766-9) increase the fidelity of mRNA half-life measurements compared to experiments with non-specific inhibitors (Ross, J., 1995, Microbiol. Rev. 59,423-50). One concern in determining insulin secretion dynamics with the Tet-responsive system is the pharmacokinetics of DOX. It has been shown that the Tet-Off system and its transcription repressor tetracycline can be applied to measure the stability of a spliced intron with a half-life as low as 6 minutes (Clement, et al., 1999, RNA 5:206-20). Hence, it appears that tetracycline quickly diffuses into cells and blocks transcription. It is expected that DOX, a tetracycline isomer and analogue, would have similar kinetics in regulating insulin gene expression in HepG2 cells However, the reverse process of decline of intracellular DOX concentration may be more complicated since, besides diffusion out, processes such as dissociation of DOX from the DOX-protein complex, distribution and accumulation of DOX in organelles, and metabolism of DOX may be occurring and contributing to the delays in insulin secretion down-regulation exhibited by the Tet-On system (FIG. 4). It is possible that with a metabolizable secretagogue, e.g., glucose, the intrinsic kinetics of transcription would be closer to the kinetics of secretion, especially during the down-regulation process.

In FIG. 4, two DOX square waves were applied to induce the Tet-On system, and obtained a 5-fold increase of insulin secretion from the single copy plasmid. An 8-hour induction was performed with the same Tet-On system, and obtained an approximately 30-fold increase of insulin secretion. This result is similar to the findings of Gossen et al. (1995, Science 268:1766-9) using luciferase as the reporter to test the kinetics of the Tet-On system. Due to the stability of the 1 copy PPI mRNA plasmid, there was no decline in insulin secretion rate during the two 7 hour DOX-free basal periods. However, the increase in insulin secretion from the second induction was significantly lower than the first. If the experiment continued in the same fashion, it is expected that the insulin secretion would not exhibit any net increase after some maximum, as any (small) additional increase in secretion rate upon induction would be compensated by a decline during the subsequent basal period.

Example 3

Translation Inhibition Indicates Role of NMD in Insulin Secretion Dynamics

Translation Inhibition Test

Tet-Off transfected HepG2 cells were washed once, then exposed to DOX-free medium with 28 μg/ml cycloheximide for 4 hours (Rajavel, K. S. & Neufeld, E. F., 2001, Mol. Cell Biol. 21:5512-9). The time of addition of cycloheximide-containing medium was time 0. To resume translation, cells were washed four times, then incubated with DOX-free, cycloheximide-free medium for two consecutive 4-hour periods. At 0, 4, 8, and 12 hours, cells were lysed for a quantitative mRNA assay.

Results

Figure 5:
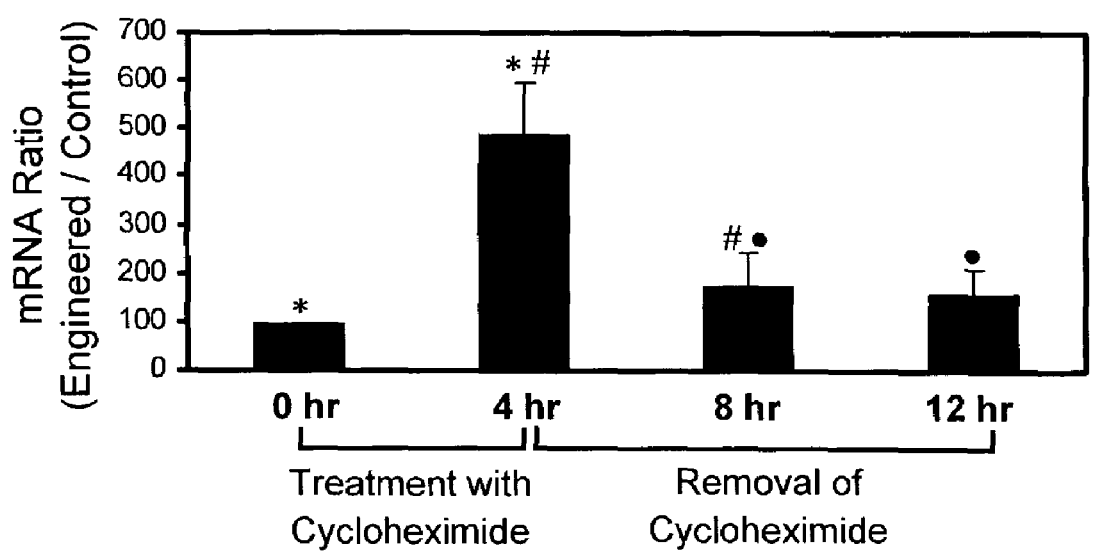
FIG. 5 shows the effect of translation on PPI mRNA stability (evidence of nonsense-mediated mRNA decay). HepG2 hepatomas were transiently co-transfected with pTet-Off and the control or engineered PPI mRNA expression plasmid. tTA mRNA was used as an internal standard for quantitative PPI mRNA assay. Cycloheximide was used as a translation inhibitor. In each independent test, the PPI mRNA ratios (engineered/control) were normalized against the sample without cycloheximide treatment (t=0), which was set at 100%. Each experiment involved 4 independent tests. * and # indicate P values<0.003, and • indicates P value=0.36. Bars indicate standard deviations.

A control experiment was performed to elucidate whether NMD was indeed involved in shortening the half-life of the engineered PPI mRNA. Since normal mRNA and nonsense mutants are distinguished from each other via translation, the effect of inhibiting translation on the levels of control and engineered PPI mRNA was examined. HepG2 hepatomas transiently transfected with control or engineered PPI mRNA under Tet-Off control were maintained in DOX-free medium and exposed to cycloheximide at time 0 (FIG. 5). The engineered/control PPI mRNA ratio at time 0 was defined as 100%. After 4 hours of cycloheximide treatment, this ratio increased to 490% compared to the cycloheximide-free culture. Upon withdrawing cycloheximide to resume translation, the engineered/control PPI mRNA ratio decreased toward the basal level.

Example 4

Effect of the Length of the Intervening DNA Sequences on mRNA Stability

Plasmids

The Tet-responsive plasmid with 1-copy of preproinsulin gene is the same as Vector F (FIG. 1) in Example 1. Constructions of the Tet-responsive plasmids with 2, 3 and 4 copies of preproinsulin gene were done by consecutively inserting 1, 2, or 3 copies of preproinsulin gene to the 3' end of preproinsulin gene in Vector F via the XbaI site, which is located next to the stop codon of preproinsulin gene.

Assays

Transcription levels, secretion of insulin, and the dynamics of insulin gene expression and insulin secretion were evaluated as described in Examples 1-3.

Results

Figure 6:
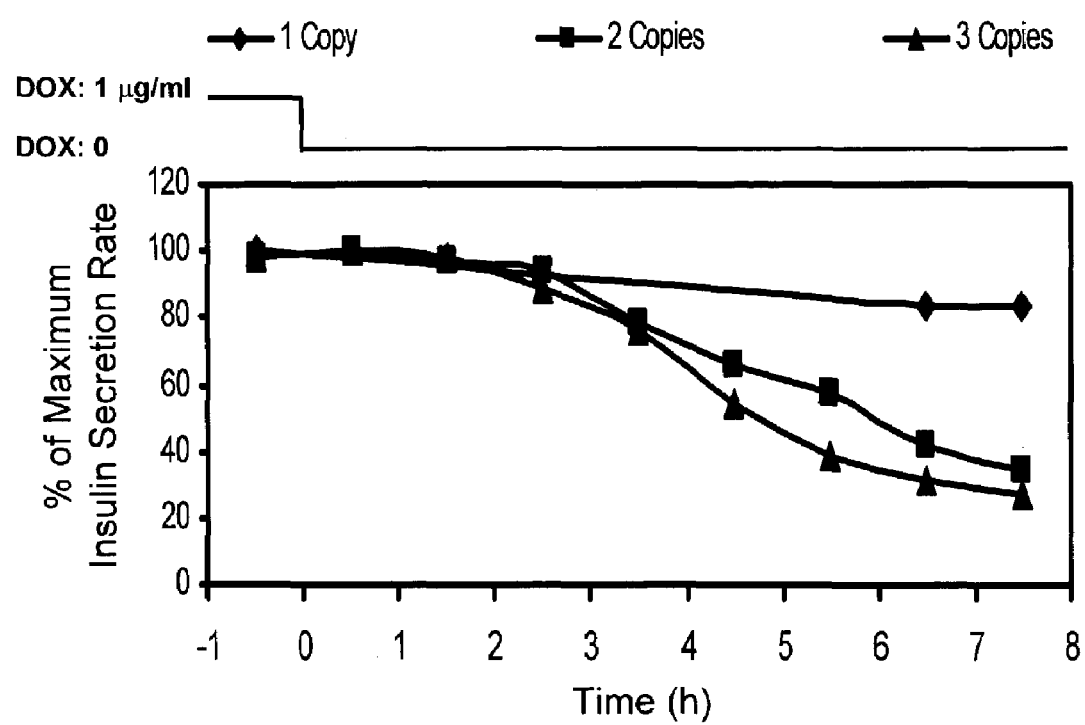
FIG. 6 shows the regulation of insulin secretion from transfected HepG2 cells using the Tet-On system with control (1-copy) and engineered (2-copy, and 3-copy) PPI containing constructs. Transcription was down-regulated by removing DOX at time 0. In each independent test, the insulin secretion rates were normalized by designating the sample with the highest rate as the calibrator and setting it at 100%.

The down-regulation in the secretion of insulin is related to the copy number of the insulin gene in the construct. As shown in FIG. 6, when DOX was removed from the Tet-On system, the constructs containing 2 and 3 copies of the preproinsulin gene demonstrated down-regulation of insulin secretion, while insulin secretion of the construct containing 1 copy of the preproinsulin gene remained relatively stable. Therefore, constructs containing more than one copy of the preproinsulin gene demonstrated a faster decline of insulin secretion following the down-regulation of transcription.

Figure 7:
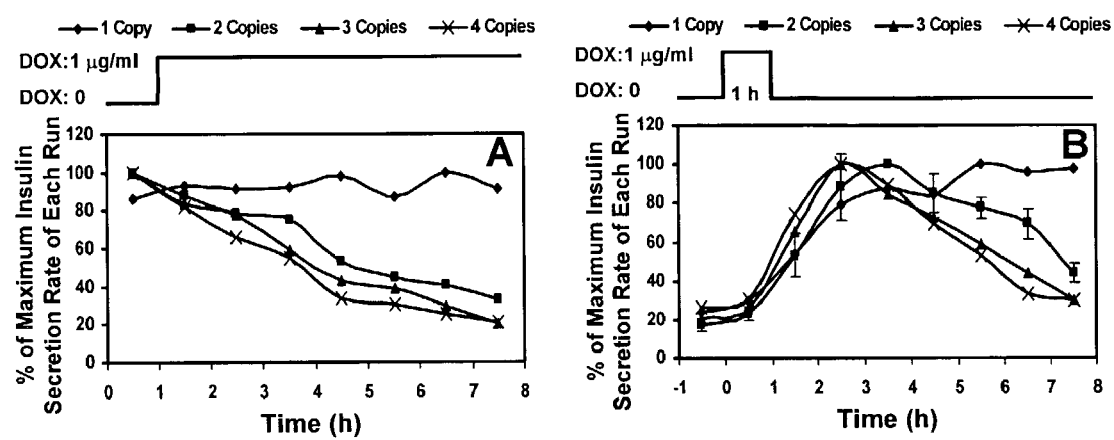
FIGS. 7A and 7B show the dynamics of down-regulation of insulin gene expression.

As shown in FIG. 7A, the Tet-Off system was used to evaluate the down-regulation of insulin secretion with constructs containing different copies (1 to 4) of the preproinsulin gene. Transcription was down-regulated by adding DOX at time 0. Compared with the one-copy control construct, systems with multiple copies of insulin gene all show faster decline of insulin secretion. FIG. 7B demonstrates the dynamics of insulin secretion with the Tet-On system when cells were exposed to a square wave of DOX induction, which mimics the effect of glucose in stimulating the transcription of insulin gene after a meal. This test indicates that the responses from the 3- and 4-copy systems are very similar. While the responses from the 3- and 4-copy systems are slightly faster than the response of the 2-copy system, the 2-copy system is noticeably faster than the 1-copy system. In addition, while the 4-copy system demonstrated an increased down-regulation in the secretion of insulin, due to the size of the constructs, the 3-copy system was easier to manipulate in the laboratory. However, it has been shown in FIGS. 7A and 7B that all multiple-copy systems tested were very effective in accelerating the down-regulation of insulin secretion compared with the one-copy control.

Figure 8:
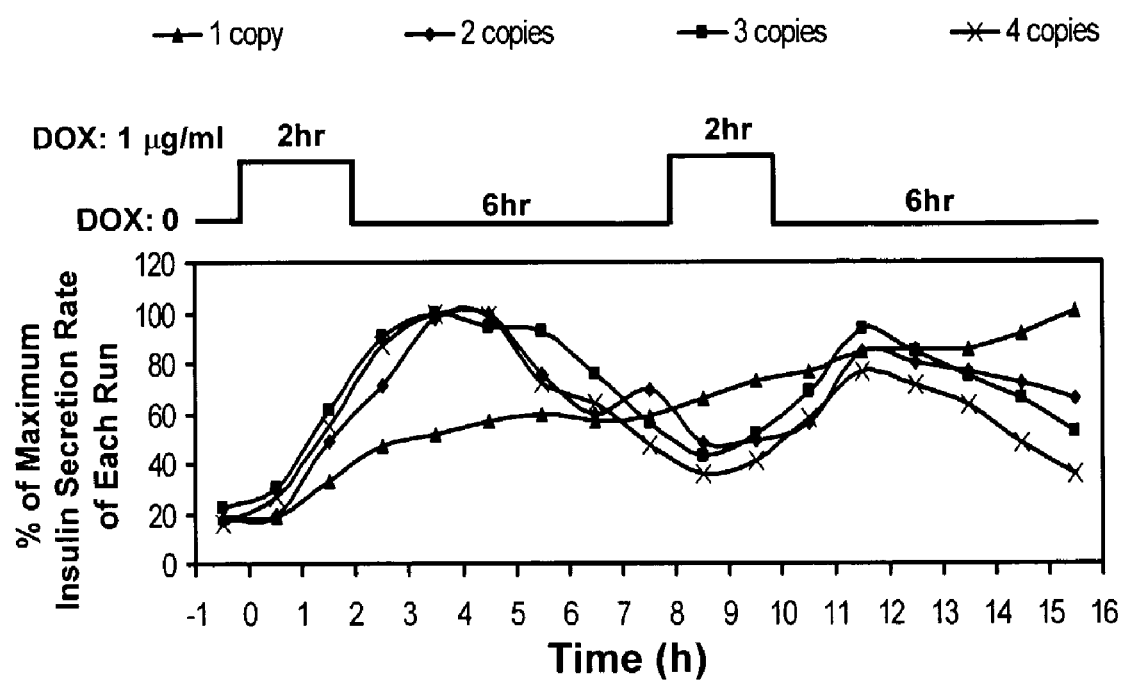
FIG. 8 shows the regulation of insulin secretion from transfected HepG2 hepatomas using the Tet-On system using constructs containing 1-4 copies of the preproinsulin gene. The cells were exposed to cycles of 2 hours of DOX induction followed by 6 hours at the basal conditions.

The dynamics of insulin secretion were examined using the 1-copy, 2-copy, 3-copy, and 4-copy constructs. The regulation of insulin secretion from transfected HepG2 hepatomas was evaluated using the Tet-On system as described in Example 2. However, rather than using a 1 hour DOX induction as described in Example 2, a 2 hour DOX induction was used, followed by 6 hours of basal conditions. The results shown in FIG. 8 indicate that insulin secretion from the multiple-copy systems can follow the square waves of DOX induction. On the other hand, the one-copy control failed to follow the square waves of DOX induction. These results indicate that placing 1, 2 or 3 copies of the preproinsulin gene downstream of the stop codon all destabilize the preproinsulin mRNA, albeit to possibly different extents, and improve the dynamics of insulin secretion.

Example 5

The Role of the Varying the Sequence of the Intervening DNA Sequences

Plasmids

The luciferase gene used to generate preproinsulin-luciferase hybrid mRNA originated from plasmid pGL3-control (Promega). To generate a SpeI site at the 5' end of the luciferase gene, a 226-bp BglII/HindIII adaptor obtained from plasmid pSE280 (Invitrogen) was used to replace the SV40 promoter fragment in pGL3-control; following by SpeI and XbaI digestions, a luciferase DNA fragment was obtained and subsequently connected to the XbaI site at the 3' end of preproinsulin gene in Vector F.

Assays

Transcription levels, secretion of insulin, and the dynamics of insulin gene expression and insulin secretion were evaluated as described in Examples 1-4.

Results

Figure 9:
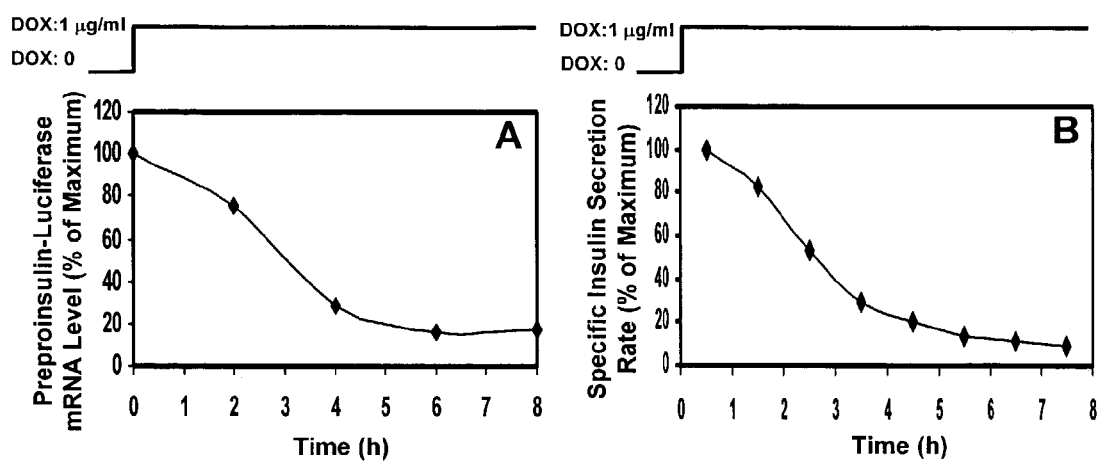
FIGS. 9A and 9B show the dynamics of down-regulation of insulin expression using the Tet-Off system, where the plasmid contained a preproinsulin-luciferase cDNA construct instead of multiple copies of the preproinsulin gene.

The down-regulation in the secretion of insulin was examined using a construct that included a preproinsulin gene operatively linked to a luciferase cDNA in an attempt to generate nonsense-mediated mRNA decay. In comparison to constructs containing multiple copies of the preproinsulin gene, this approach also creates a distance between the translation stop codon of the preproinsulin gene and the polyadenylation signal. The size of luciferase gene is 1650 bp, in comparison to the preproinsulin gene which is 360 bp in length. FIG. 9 shows the down-regulation of preproinsulin-luciferase hybrid mRNA (FIG. 9A) and insulin secretion rate (FIG. 9B) were similar to the dynamics of the three-copy system as shown in FIGS. 3A and 3B (filled squares). This result demonstrates that the fast down-regulation of insulin secretion is not limited to systems containing multiple-copies of the preproinsulin gene. When the preproinsulin gene was connected with a different DNA sequence such as the luciferase gene, a faster down-regulation of insulin expression was observed compared to the one-copy insulin control construct as shown in FIGS. 3A and 3B (open circles).

We claim:

1. A nucleic acid construct that produces a nonsense mediated mRNA transcript encoding a transcriptionally regulated insulin protein, wherein the nonsense mediated mRNA transcript has a shorter half-life than an mRNA encoding the transcriptionally regulated insulin protein that is not nonsense mediated, and wherein said nucleic acid construct comprises a nucleic acid sequence of SEQ ID NO:2, SEQ ID NO:3, or SEQ ID NO:4.

2. The nucleic acid construct of claim 1, wherein the nonsense mediated mRNA transcript comprises a sequence for a premature termination signal.

3. The nucleic acid construct of claim 2, wherein the sequence for the premature termination signal comprises a stop codon in the portion of the mRNA transcript encoding the transcriptionally regulated protein, a polyadenylation sequence and a supplementary nucleic acid sequence inserted between the stop codon and the polyadenylation sequence.

4. The nucleic acid construct of claim 3, wherein the stop codon is located approximately 350-1650 nucleotides upstream of the polyadenylation sequence.

5. The nucleic acid construct of claim 3, wherein the stop codon is located approximately 600-800 nucleotides upstream of the polyadenylation sequence.

6. The nucleic acid construct of claim 3, wherein the stop codon is located approximately 700 nucleotides upstream of the polyadenylation sequence.

7. The nucleic acid construct of claim 3, wherein the supplementary nucleic acid sequence comprises at least one copy of a preproinsulin polynucleotide.

8. The nucleic acid construct of claim 3, wherein the supplementary nucleic acid sequence comprises approximately two copies of a preproinsulin polynucleotide.

9. The nucleic acid construct of claim 1, comprising the nucleic acid sequence of SEQ ID NO:2.

10. The nucleic acid construct of claim 1, comprising the nucleic acid sequence of SEQ ID NO:3.

11. The nucleic acid construct of claim 1, comprising the nucleic acid sequence of SEQ ID NO:4.

12. An isolated, mammalian non-β cell comprising a heterologous nucleic acid construct which produces a nonsense mediated mRNA transcript encoding a transcriptionally regulated insulin protein, wherein said heterologous nucleic acid construct comprises a nucleic acid sequence of SEQ ID NO:2, SEQ ID NO:3, or SEQ ID NO:4, and wherein the transcriptionally regulated protein is secreted by the cell and the nonsense mediated mRNA insulin transcript has a shorter half-life than an mRNA encoding the transcriptionally regulated insulin protein that is not nonsense mediated.

13. The cell of claim 12, wherein the nonsense mediated mRNA transcript comprises a sequence for a premature termination signal.

14. The cell of claim 13, wherein the sequence for the premature termination signal comprises a stop codon in the portion of the mRNA transcript encoding the transcriptionally regulated insulin protein, a polyadenylation sequence and a supplementary nucleic acid sequence inserted between the stop codon and the polyadenylation sequence.

15. The cell of claim 12, wherein the heterologous nucleic acid construct comprises the nucleic acid sequence of SEQ ID NO:2.

16. The cell of claim 12, wherein the heterologous nucleic acid construct comprises the nucleic acid sequence of SEQ ID NO:3.

17. The cell of claim 12, wherein the heterologous nucleic acid construct comprises the nucleic acid sequence of SEQ ID NO:4.

18. The cell of claim 14, wherein the stop codon is located approximately 350-1650 nucleotides upstream of the polyadenylation sequence.

19. The cell of claim 14, wherein the stop codon is located approximately 600-800 nucleotides upstream of the polyadenylation sequence.

20. The cell of claim 14, wherein the stop codon is located approximately 700 nucleotides upstream of the polyadenylation sequence.

21. The cell of claim 14, wherein the supplementary nucleic acid sequence comprises at least one copy of a preproinsulin polynucleotide.

22. The cell of claim 14, wherein the supplementary nucleic acid sequence comprises two copies of a preproinsulin polynucleotide.

23. The cell of claim 12, wherein the cell is a human cell.

24. The cell of claim 12, wherein the cell is a hepatic cell.

25. A method of treating a patient in need thereof, comprising administering to the patient a therapeutically effective amount of the cell of claim 12.

26. The method of claim 25, wherein the disease is diabetes.

27. A method for down-regulating secretion of a transcriptionally regulated insulin protein comprising:
    a) introducing a heterologous nucleic acid construct into a cell, wherein said heterologous nucleic acid construct comprises a nucleic acid sequence of SEQ ID NO:2, SEQ ID NO:3, or SEQ ID NO:4, and wherein the heterologous nucleic acid construct transcribes a nonsense mediated mRNA transcript which encodes the transcriptionally regulated protein; and
    b) expressing the heterologous nucleic acid construct to produce the nonsense mediated mRNA transcript encoding the transcriptionally regulated insulin protein, such that the transcriptionally regulated protein is secreted by the cell and the nonsense mediated mRNA transcript has a shorter half-life than an mRNA encoding the transcriptionally regulated insulin protein that is not nonsense mediated;
    to thereby down-regulate secretion of the insulin protein.

28. The method of claim 27, wherein the transcriptionally regulated protein is human insulin protein.

29. The method of claim 27, wherein the heterologous nucleic acid construct comprises a sequence of SEQ ID NO:2 that encodes preproinsulin.

30. The method of claim 27, wherein the nonsense mediated mRNA transcript comprises a sequence for a premature termination signal.

31. The method of claim 30, wherein the sequence for the premature termination signal comprises a stop codon of the mRNA transcript encoding the transcriptionally regulated insulin protein, a polyadenylation sequence and a supplementary nucleic acid sequence inserted between the stop codon and the polyadenylation sequence.

32. The method of claim 31, wherein the stop codon is located approximately 350-1650 nucleotides upstream of the polyadenylation sequence.

33. The method of claim 31, wherein the stop codon is located approximately 600-800 nucleotides upstream of the polyadenylation sequence.

34. The method of claim 31, wherein the stop codon is located approximately 700 nucleotides upstream of the polyadenylation sequence.

35. The method of claim 31, wherein the supplementary nucleic acid sequence comprises one or more preproinsulin protein coding sequences.

36. The method of claim 27, wherein the cell is selected from the group consisting of an animal cell, a plant cell, a bacterial cell, a protozoal cell, or a fungal cell.

37. The method of claim 27, wherein the cell is an animal cell.

38. The method of claim 27, wherein the cell is a human cell.

39. The method of claim 27, wherein the cell is a hepatic cell.

40. The method of claim 27, wherein the cell is a non-β cell.

41. A cell produced using the method of claim 27.

42. A method of treating a patient in need thereof, comprising administering to the patient a therapeutically effective amount of the cell of claim 41.

43. The method of claim 42, wherein the patient has diabetes.

44. A method of modulating the secretion dynamics of insulin by promoting degradation of preproinsulin mRNA, comprising introducing a heterologous nucleic acid into a non-β cell, wherein the heterologous nucleic acid comprises a preproinsulin-encoding polynucleotide of SEQ ID NO:2, SEQ ID NO:3, or SEQ ID NO:4 operatively linked to a promoter, and transcribes a nonsense mediated mRNA transcript which encodes the transcriptionally regulated insulin protein, wherein the nonsense mediated mRNA transcript comprises a sequence for a premature termination signal, and wherein the nonsense mediated mRNA transcript has a shorter half life than a mRNA encoding the transcriptionally regulated insulin protein that is not nonsense mediated, thereby modulating the secretion dynamics of insulin by promoting degradation of preproinsulin mRNA.

45. The method of claim 44, wherein the sequence for the premature termination signal comprises a stop codon in the preproinsulin-encoding polynucleotide, a polyadenylation sequence and a supplementary nucleic acid sequence inserted between the stop codon and the polyadenylation sequence.

46. The method of claim 45, wherein the stop codon is located approximately 350-1650 nucleotides upstream of the polyadenylation sequence.

47. The method of claim 45, wherein the stop codon is located approximately 600-800 nucleotides upstream of the polyadenylation sequence.

48. The method of claim 45, wherein the stop codon is located approximately 700 nucleotides upstream of the polyadenylation sequence.

49. The method of claim 45, wherein the supplementary nucleic acid sequence comprises at least one copy of a preproinsulin polynucleotide.

50. The method of claim 45, wherein the supplementary nucleic acid sequence comprises two copies of a preproinsulin polynucleotide.

51. The method of claim 44, wherein the non-β cell is a human cell.

52. The method of claim 44, wherein the non-β cell is a hepatic cell.

53. A cell produced using the method of claim 44.

54. A method of treating a patient in need thereof comprising administering to the patient a therapeutically effective amount of the cell of claim 53.

55. The method of claim 54, wherein the disease is diabetes.

* * * * *